(12) United States Patent
Richards-Kortum et al.

(10) Patent No.: US 6,593,101 B2
(45) Date of Patent: Jul. 15, 2003

(54) ENHANCING CONTRAST IN BIOLOGICAL IMAGING

(75) Inventors: Rebecca R. Richards-Kortum, Austin, TX (US); Andrés F. Zuluaga, Boston, MA (US); Rebekah Drezek, Houston, TX (US); Colin Smithpeter, Albuquerque, NM (US); Tom Collier, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/821,843

(22) Filed: Mar. 28, 2001

(65) Prior Publication Data

US 2002/0127632 A1 Sep. 12, 2002

Related U.S. Application Data

(60) Provisional application No. 60/192,541, filed on Mar. 28, 2000.

(51) Int. Cl.[7] ............................ C12Q 1/02; G01N 33/53; A61B 10/00
(52) U.S. Cl. ...................... 435/29; 435/283.1; 435/968; 600/478; 424/9.6
(58) Field of Search ..................... 435/29, 283.1, 435/968; 600/478; 424/9.6

(56) References Cited

U.S. PATENT DOCUMENTS

| | | | |
|---|---|---|---|
| 4,300,570 A | 11/1981 | Stafl ........................... 128/665 |
| 5,116,328 A | 5/1992 | Dyer et al. .................. 604/289 |
| 5,370,119 A | * 12/1994 | Mordon et al. ............. 128/654 |
| 5,648,216 A | 7/1997 | Hershfield et al. ............. 435/6 |
| 5,697,373 A | 12/1997 | Richards-Kortum et al. ........................... 128/664 |
| 5,836,877 A | 11/1998 | Zavislan ..................... 600/407 |
| 5,842,995 A | 12/1998 | Mahadevan-Jansen et al. .. 600/473 |
| 5,845,639 A | * 12/1998 | Hochman et al. ......... 128/653.1 |
| 6,187,289 B1 | 2/2001 | Richards-Kortum et al. . 424/9.8 |
| 6,370,422 B1 | * 4/2002 | Richards-Kortum et al. ........................... 600/478 |
| 6,395,257 B1 | * 5/2002 | Achilefu et al. ............. 424/9.6 |

FOREIGN PATENT DOCUMENTS

| | | |
|---|---|---|
| WO | WO 99/20313 | 4/1999 |
| WO | WO 99/47041 | 9/1999 |
| WO | WO 99/57507 | 11/1999 |
| WO | WO 01/72215 A1 * | 10/2001 |

OTHER PUBLICATIONS

Alfano et al., "Fluorescence Spectra from Cancerous and Normal Human Breast and Lung Tissues," *IEEE Journ. Quant. Electron.*, QE–23:1806–1811, 1987.

Bail et al., "Optical coherence tomography with the "spectral radar": fast optical analysis in volume scatterers by short–coherence interferometry," presented at Photon Propagation in Tissues II, SPIE, 2925:298–303, 1996.

Barton et al., "Investigating pulsed dye laser–blood vessel interaction with color Doppler optical coherence tomography," *Optics Express*, 3:251–256, 1998.

Bernasconi et al., "High–resolution, high–speed photorefractive incoherent–to–coherent optical converter," *Optics Letters*, vol. 24, pp. 199–201, 1999.

(List continued on next page.)

*Primary Examiner*—Louise N. Leary
(74) *Attorney, Agent, or Firm*—Fulbright & Jaworski, LLP

(57) ABSTRACT

Methods for enhancing contrast during imaging to assess cell and nuclear morphology of a sample. A contrast agent such as acetic acid, toluidine blue, hypertonic saline, hypotonic saline, Lugol's iodine, an absorbing dye, a liposome, or a contrast agent linked to a marker are applied to a sample. The sample is analyzed with an imaging device to create image data, and the sample is diagnosed using the image data.

38 Claims, 10 Drawing Sheets

OTHER PUBLICATIONS

Bigio and Mourant, "Ultraviolet and visible spectroscopies for tissue diagnostics: fluorescence spectroscopy and elastic–scattering spectroscopy. [Review]," *Physics in Medicine and Biology*, 42:803–814, 1997.

Bohnke and Masters, "Confocal microscopy of the cornea. [Review]," *Progress in Retinal and Eye Research*, 18:553–628, 1999.

Bohorfoush, "Tissue spectroscopy for gastrointestinal diseases. [Review]," *Endoscopy*, 28:372–380, 1996.

Boppart et al., "Noninvasive assessment of the developing Xenopus cardiovascular system using optical coherence tomography," *PNAS USA.*, 94:4256–4261, 1997.

Bouma and Tearney, "Power–efficient nonreciprocal interferometer and linear–scanning fiber–optic catheter for optical coherence tomography," *Optics Letters*, 24:531–533, 1999.

Bouma et al., "High–Resolution Optical Coherence Tomographic Imaging Using a Mode–Locked Ti:Al2O3 Laser Source," *Opt. Lett.*, 20:1486–88, 1995.

Brezinski et al., "Optical biopsy with optical coherence tomography," *Annals of the New York Academy of Sciences*, 838:68–74, 1998.

Chinn et al., "Optical Coherence Tomography Using a Frequency–Tunable Optical Source," *Optics Letters*, 22:340–342, 1997.

Clivaz et al., "High–Resolution Reflectometry in Biological Tissues," *Opt. Lett.*, 17:4, 1992.

Clivaz et al., "Optical Low Coherence Reflectometry with 1.9 μm Spatial Resolution," *Electron. Lett.*, 28:1553–1555, 1992.

Colston et al., "Optical Coherence Tomography for Diagnosing Periodontal Disease," presented at Lasers in Denistry III, San Jose, CA, SPIE, 2973:216–220, 1997.

Cothren et al., "Gastrointestinal tissue diagnosis by laser–induced fluorescence spectroscopy at endoscopy," *Gastrointest. Endosc.*, 36:105–111, 1990.

Danforth's Obstetrics and Gynecology, $7^{th}$ Edition, pp. 918–921, 1994.

de Boer et al., "Determination of the depth–resolved Stokes parameters of light backscattered form turbid media by use of polarization–sensitive optical coherence tomography," *Optics Letters*, 24:300–302, 1999.

de Boer et al., "Imaging thermally damaged tissue by polarization sensitive optical coherence tomography," *Optics Express*, 3:212–218, 1998.

Derenzini et al., "Nucleolar function and size in cancer cells," *Am. J. of Pathology*, 152:1291–1297, 1998.

Drezek et al., "Laser scanning confocal microscopy of cervical tissue before and after application of acetic acid," *Am. J. Obstetrics and Gynecology*, 182:1135–1139, 2000.

Drezek et al., "Light scattering from cells: Finite difference time domain modeling and goniometric measurements of light scattering form cells," *Applied Optics*, 38:3651–3661, 1999.

Dunn and Richards–Kortum, "Three–dimensional computation of light scattering from cells," *IEEE Journal of Selected Topics in Quantum Electronics*, 2:898–905, 1997.

Fahey et al., "Meta–analysis of Pap Test Accuracy," *American Journal of Epidemiology*, 141:680–689, 1995.

Feldchtein et al., "Endoscopic applications of optical coherence tomography," *Optics Express*, 3:257–270, 1998.

Feldchtein et al., "In vivo OCT imaging of hard and soft tissue of the oral cavity," *Optics Express*, 3:239–250, 1998.

Fercher et al., "Eye–Length Measurement by Interferometry with Partially Coherent Light," *Opt. Lett.*, 13:186–188, 1988.

Fercher et al., "Measurement of intraocular Optical Distances Using Partially Coherent Laser Light," *Journal of Modern Optics*, 38:1327–1333, 1991.

Fercher et al., "Measurement of Optical Distances by Optical Spectrum Modulation," presented at SPIE, 2083–263–267, 1994.

Ficsor et al., "Enhancing cervical cancer detection using nucleic acid hybridization and acetic acid tests," *Nurse Practitioner*, 15:26–30, 1990.

Fujimoto et al., "Optical Biopsy and Imaging Using Optical Coherence Tomography," *Nature Medicine*, 1:970–972, 1995.

Haberland et al., "Optical Coherence Tomography of Scattering Media Using Frequency Modulated Continuous Wave Techniques with Tunable Near–infrared Laser," Presented at SPIE, 1997.

Hausler and Lindner, ""Coherence Radar" and "Spectral Radar"—New Tools for Dermatological Diagnosis," *Journal of Biomedical Optics*, 3:21–31, 1998.

Hee et al., "Optical coherence tomography for ophthalmic imaging," *IEEE Eng Med Biol*, 14:67–76, 1995.

Huang et al., "Optical Coherence Tomography," *Science*, 254:1178–1181, 1991.

Hung et al., "Autofluorescence of normal and malignant bronchial tissue," *Las. Surg. Med.*, 11:99–105, 1991.

Inoue et al., In: "Handbook of Biological Confocal Microscopy,". New York: Plenum Press, Chapters 1–4, 7–9, 1995.

Izatt et al., "Micron–Resolution Biomedical Imaging with Optical Coherence Tomography," *Opt. Photon. News*, 4:14, 1993.

Izatt et al., "Ophthalmic Diagnostics using Optical Coherence Tomography," *Proc. Soc. Photo–Opt. Instrum. Eng.*, 1877:136–143, 1993.

Izatt et al., "Optical Coherence Microscopy in Scattering Media," *Opt. Lett.*, 19:590–592, 1994.

Izatt et al., "Optical Coherence Tomography and Microscopy in Gastrointestinal Tissues," presented at Advances in Optical Imaging and Photon Migration, Orlando, FL, 1996.

Izatt, et al., "Micrometer–Scale Resolution Imaging of the Anterior Eye with Optical Coherence Tomography," *Arch. Ophthalmol.*, 112:1584–1589, 1995.

Kelloff et al., "Intermediate Biomarkers of Precancers and their Application in Chemoprevention," *Journal of Cellular Biochemistry*, vol. Suppl(16G):15–21, 1992.

Lam et al., "Detection and localization of early lung cancer by imaging techniques.," *Chest*, 113:696–702, 1993.

Liu et al., "Superficial carcinomas of the esophagus and gastric carida. A clinicopathological analysis of 141 cases," *Chinese Medical Journal*, 108:754–759, 1995.

Martin et al., "The application of toluidine blue as a diagnostic adjunct in the detection of epithelial dysplasia," *Oral Surgery, Oral Medicine, Oral Pathology Oral Radiology and Endodontics*, 85:444–446, 1998.

Meyer et al., "Endoscopic detection of early esophageal cancer in a high–risk population: does Lugol staining improve videoendoscopy?," *Gastrointestinal Endoscopy*, 45:480–484, 1997.

Mitchell, "The Accuracy of Colposcopy," *Clinical Consultation in Obstetrics and Gynecology*, 6:70–73, 1994.

Nakanishi et al., "The clinicopathologic significance of small areas unstained by Lugol's iodine in the mucosa surrounding resected esophageal carcinoma: an analysis of 147 cases," *Cancer*, 82:1454–1459, 1998.

Nishioka, "Laser–induced fluorescence spectroscopy. [Review]," *Gastrointestinal Endoscopy Clinics of North America*, 4:313–326, 1994.

Pan et al., "Low–Coherence Optical Tomography in Turbid Tissue: Theoretical Analysis," *Appl. Opt.*, 34:6564–6574, 1995.

Pitris et al., "High resolution imaging of gynecologic neoplasms using optical coherence tomography," *Obstetrics and Gynecology*,93:135–139, 1999.

Pitris et al., "In–vivo catheter–based imaging with optical coherence tomography," presented at Advances in Optical Imaging and Photon Migration, Orlando, FL, 1998.

Puliafito et al., "Imaging of Macular Diseases with Optical Coherence Tomography," *Ophthalmol.*, 102:217–229, 1995.

Rajadhyaksha et al., "In vivo confocal scanning laser microscopy of human skin II: advances in instrumentation and comparison with histology," *J. Investigative Dermatology*, 113:293–303, 1999.

Rajadhyaksha et al., "In–vivo confocal scanning laser microscopy of human skin: melanin provides strong contrast," *Journal of Investigative Dermatology*, 104:946–952, 1995.

Ramanujam et al., "Fluorescence Spectroscopy: a Diagnostic Tool for Cervical Intraepithelial Neoplasia (CIN)," *Gynecologic Oncology*, 52:31–38, 1994.

Reitze et al., "Low Coherence Imaging of Cerebral Structures in Vivo," presented at Coherence Domain Optical Methods in Biomedical Science and Clinical Applications, San Jose, CA, 1997.

Richards–Kortum and Sevick–Muraca, "Quantitative Optical Spectroscopy for Tissue Diagnosis," *Annual Review in Physical Chemistry*, 47:555–606, 1996.

Riddell, "Early detection of neoplasia of the esophagus and gastroesophageal junction," *Am. J. Gastroenterology*, 91:853–863, 1996.

Rollins et al., "Real–time in vivo imaging of human gastrointestinal ultrastructure by use of endoscopic optical coherence tomography with a novel efficient interferometer design," *Optics Letters*, 24:1358–1360, 1999.

Rollins et al., "In vivo video rate optical coherence tomography," *Optics Express*, 3:219–229, 1998.

Roy et al., "Diagnostic Fluorescence Spectroscopy of Oral Mucosa," presented at Lasers and Surgery: Advanced Characterization, Therapeutics and Systems IV, SPIE, 1995.

Schmitt et al., "Confocal Microscopy in Turbid Media," *J. Opt. Soc. Am. A*, 11:2226–2235, 1994.

Schmitt et al., "Measurement of Optical Properties of Biological Tissues by Low–Coehrence Reflectometry," *Appl. Opt.*, 32:6032–6042, 1993.

Schmitt, "OCT elastography: imaging microscopic deformation and strain of tissue," *Optics Express*, 6:199–211, 1998.

Schomacker et al., "Ultraviolet Laser–Induced Fluorescence of Colonic Tissue: Basic Biology and Diagnostic Potential," *Las. Surg. Med.*, 12:63–78, 1992.

Schultz and Skelton, "Value of acetic acid screening for flat genital condlyomata in men," *Journal of Urology*, 139:777–779, 1988.

Schuman et al., "Quantification of Nerve Fiber Thickness in Normal and Glaucomatous Eyes using optical Coherence Tomography: A Pilot Study," *Arch. Ophthalmol.*, 113:586–596, 1995.

Sergeev et al., "In–vivo Endoscopic OCT Imaging of Precancer and Cancer States of Human Mucosa," *Optics Express*, vol. 1, pp. 432–440, 1997.

Sergeev et al., "Melanin effect on light scattering in tissues: from electrodynamics of living cell to OCT imaging," presented at Coherence Domain Optical Methods in Biomedical Science and Clinical Applications, 1997.

Silverman, Jr., "Early diagnosis of oral cancer," *Cancer*, 62:1796–1799, 1988.

Sloot et al., "Osmotic response of lymphocytes measured by means of forward light scattering: Theoretical considerations," *Cytometry*, 9:636–641, 1988.

Smithpeter et al., "Near real time confocal microscopy of cultured amelanotic cells: sources of signal, contrast agents and limits of contrast," *J. Biomedical Optics*, 3:429–436, 1998.

Smithpeter, "Fiber optic confocal imaging for in vivo detection and diagnosis of pre–cancerous lesions," University of Texas at Austin, Dissertation, 1997.

Swanson et al., "High Speed Optical Coherence Domain Reflectometry," *Opt. Lett.*,17:151–153, 1992.

Swanson et al., "In Vivo retinal imaging by optical coherence tomography," *Opt. Lett.*, 18:1864–1866, 1993.

Tanifuji et al., "Functional imaging of the brain by using light," *Oyo Buturi*, 68:997–1007, 1999, Abstract Attached.

Tearney et al., "Endoscopic Optical Coherence Tomography," presented at Optical Tomography and Spectroscopy of Tissue: Instrumentation, Model, and Human Studies II, San Jose, CA, 1997.

Tearney et al., "Scanning Single–Mode Fiber Optic Catheter–Endoscope for Optical Coherence Tomography," *Opt. Lett.*, 21:543–545, 1996.

Van Le et al., "Acetic acid visualization of the cervix to detect cervical dysplasia," *Obstetrics and Gynecology*, 81:293–295, 1993.

Wang et al., "Quantitative laser scanning confocal autofluorescence microscopy of normal, premalignant, and malignant colonic tissues," *IEEE Transactions on Biomedical Engineering*, 46:1246–1252, 1999.

Webb et al., "Confocal Laser Scanning Ophtalmoscope, "*Applied Optics*, 26:1492–1499, 1987.

Youngquist et al., "Optical Coherence Domain Reflectometry: A New Optical Evaluation Technique," *Opt. Lett.*, 12:158–160, 1987.

Zucker et al., "Confocal laser scanning microscopy of rat follicle development," *J. of Histochemistry and Cytochemistry*, 48:781–791, 2000.

Zuluaga, "Development of a cervical probe for optical coherence imaging in–vivo," in Dept. of Electrical and Computer Engineering. Austin: University of Texas at Austin, pp. 49, 1998.

\* cited by examiner

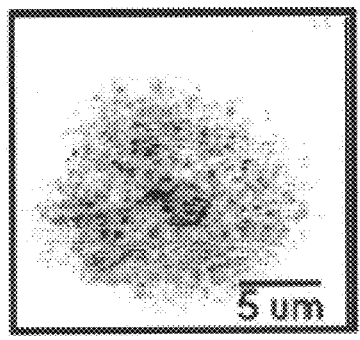
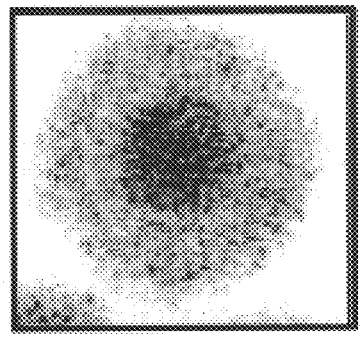
*FIG. 1A*  *FIG. 1B*
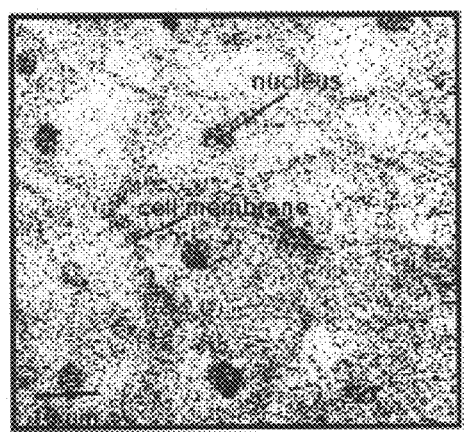
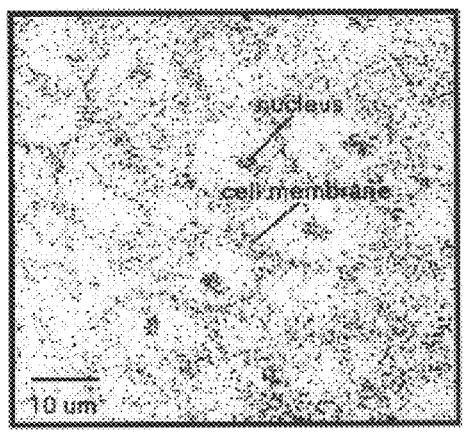
*FIG. 2A*  *FIG. 2B*

ENHANCING CONTRAST IN BIOLOGICAL IMAGING

This application claims priority to provisional patent application Serial No. 60/192,541 filed Mar. 28, 2000, entitled, "Enhancing Contrast in Biological Imaging" by Rebecca R. Richards-Kortum, Andrés F. Zuluaga, Rebekah Drezak, Colin Smithpeter, and Tom Collier. The entire text of the above-referenced disclosure is specifically incorporated by reference herein without disclaimer.

The government may own rights in the present invention pursuant to grant number 1R55CA73920-01 from the National Institutes of Health.

BACKGROUND OF THE INVENTION

1. Field of the Invention

The present invention relates generally to the field of imaging. More particularly, it concerns techniques for enhancing contrast in optical techniques for biological applications.

2. Description of Related Art

Photonic technologies are playing an increasingly important role in biomedical diagnostics, resulting from improvements in optical instrumentation and an improved understanding of the interaction between light and biological tissues. At least two techniques have contributed to recent progress in biomedical optical imaging and disease diagnosis: (1) biological characterization techniques based on optical spectroscopy, and (2) imaging such as confocal microscopy and optical coherence tomographic (OCT), derived from interferometric and ultrafast optical technologies. In the first technique, highly specific in vivo identification of biological moieties at the molecular level may be accomplished using unique spectral signatures of intrinsic or extrinsic tissue chromophores. In the second, near-histological resolution imaging of sub-surface tissue microstructure may be performed even in highly scattering biological tissues by high-contrast rejection of multiply-scattered light.

Much work has been done to develop photonic technologies for diagnosing cancers and pre-cancers due to the fact that cancer is one of the leading causes of death in the United States and in the world. In the United States alone, deaths from cancer were estimated to number 560,000 in 1997. Currently, diagnosis and treatment of cancer follow histopathologic evaluation of directed biopsies. However, the tissue removal necessitated by these techniques not only may alter the progression of disease but is also very costly. Improving the capability for in-situ monitoring of disease progression may greatly enhance the ability to detect and treat cancer and pre-cancer.

In women, cervical cancer alone will account for an estimated 14,500 new cases and 4,800 deaths in 1997. Its precursor, cervical intraepithelial neoplasia (CIN), refers to a tumor growth in the cervical epithelium. Such growth is believed to originate from a single mutant cell near the basal layer of the epithelium. Rather than follow the normal maturation process, the mutant cell continues to divide without control. This results in a growing, undifferentiated group of cells, which gradually spreads from the basal layer to the surface layer of the epithelium. The disease is considered pre-invasive when it is confined to the epithelium. If detected at this stage, the disease is curable. Eventually, the basal layer may be compromised, and the transformed cells may invade the stroma. At this stage, the disease is considered invasive.

Early detection of CIN has been crucial to the reduction of the mortality caused by cervical cancer over the last decades. Currently, cytologic techniques are of widespread use in the screening of gynecologic cancers. Unfortunately, the accuracy of such techniques is not optimal. In one study of the accuracy of the Papanicolau test, it was found that sensitivity ranged from 11 to 99% and specificity from 14 to 97%. If an abnormal Pap smear is detected, further examination is often performed using a low power microscope called a colposcope. Colposcopy is used to identify the extent and grade of the lesion, and to direct any biopsies to be taken. While highly sensitive, colposcopy is unfortunately not very specific. This means that a large number of normal sites, usually inflammation or HPV infection, may be classified as diseased. Colposcopy is only performed by trained experts, making the cost of more widespread screening with this method prohibitive. In view of the above, there is a need for more accurate, automated screening and diagnostic tools to identify cervical precancers.

Work done in the area of optical spectroscopy has been aimed at aiding in the diagnosis of cancer and pre-cancer not only in gynecologic tissue but also in other kinds of tissue. Some techniques attempt to classify the tissue being probed by effectively assessing its biochemical and morphologic composition as evidenced by the light reflected, absorbed or emitted as Raman or fluorescence signals. Such techniques attempt to provide additional information that will result in improved in-situ diagnosis, allowing for better diagnostic performance by less-specialized personnel.

Confocal microscopy is an imaging technique well-suited for the evaluation of thick, turbid samples due to its ability to reject light from outside the focal volume. The technique has been used extensively in vitro and applications for in vivo and endoscopic use have been developed. Confocal microscopy has a spatial resolution on the order of 1 to 2 microns, allowing it to resolve single cells and their nuclei. This makes it a potential tool for aiding diagnosis since it may provide near-histologic resolution images in vivo. However, confocal imaging is only possible at depths of several hundred microns, as image quality is degraded by wavefront aberrations induced by the scattering in the tissue, and contrast may be reduced by multiply scattered, detected photons generated outside the confocal volume. There is therefore a need for techniques for enhancing contrast so as to improve confocal microscopy imaging.

Optical coherence tomography (OCT) is another imaging technique that may overcome at least some of the problems associated with multiple scattering, allowing it to image sub-surface structure in tissue. OCT detects very faint reflections of laser light directed into the tissue and determines at what depth these reflections occurred. This results in an image of the relative reflectivity of the tissue below the surface. This is related to the properties of individual cells as well as the overall structure of the tissue, both of which may change in the presence of disease.

With OCT, tomographic images of sub-surface biological microstructure may be obtained with ~10 $\mu$m spatial resolution. The heterodyne optical detection scheme inherent to OCT provides sensitivity to backscattered signals as small as one part in $10^{11}$ of the incident optical power; thus, extremely faint reflections may be visualized. In OCT, the specimen to be interrogated may be placed in the sample arm of an interferometer illuminated with a low-coherence light source. Interference between light returning from the reference arm and light scattered from internal sample reflections occurs only when the optical path lengths in both arms of the interferometer are matched to within the source coherence length. Thus, scanning the reference arm while monitoring the envelope of the interferometric signal generates a map of tissue reflectivity versus optical depth or "A-scan," with axial resolution given by the coherence length. Cross-sectional images of tissue backscatter may be built from sequential A-scans obtained while scanning the probe beam across the tissue surface. Resulting two-dimensional data sets may be plotted as gray-scale images.

The initial clinical application of OCT was for high-resolution imaging of intraocular structure. OCT is well suited to ophthalmology because it is non-contact, easily adaptable to existing ophthalmic instrumentation, and the axial image resolution is independent of the working distance. A growing number of studies of OCT imaging in non-transparent media have also been reported. In vitro and in vivo studies have reported OCT imaging in the skin, teeth, and brain, as well as in vascular, respiratory, and gastrointestinal tissues. Recent technical advances in image acquisition time and probe miniaturization have produced the first studies on catheter and endoscopic OCT imaging in living animals and humans.

Using a catheter approximately 1 mm in diameter capable of insertion in an endoscope accessory channel, in vivo images of human esophagus, larynx, stomach, urinary bladder, and uterine cervix have been reported. Epithelial invasion of the basement membrane was distinctly visible in images of early cancers, implying that the technique may be promising for early diagnosis of tumors and precise guiding of excisional biopsy.

The success of OCT and other imaging techniques underscore many advantages in imaging subsurface morphology. However, OCT resolution is lower than that of light microscopy, the current gold standard in the tissue malignancy assessment following biopsy. Attaining the level of resolution necessary to make malignancy assessments in human epithelial tissue samples by nuclear size determination is currently unattainable through OCT. Therefore, if such assessments are to be done with OCT in-vivo, further differentiation techniques must be developed.

Despite the promise of imaging techniques discussed above, and their application to the detection of, for instance, cancer, little is understood about how to achieve optimal contrast in such images, particularly in highly-scattering tissues where early cancers and pre-cancers develop. The primary sources of signal in traditional OCT images arise from mismatches in tissue index of refraction; however, little is known about the wavelength-dependent microscopic fluctuations in the tissue refractive index and how those vary in normal and pathologic tissues.

In view of the above, it is apparent that a need exists for developing techniques to enhance contrast in different fields of biomedical imaging so that, for instance, cancers and pre-cancers may be diagnosed earlier and more easily, with greater accuracy.

SUMMARY OF THE INVENTION

In one respect, the invention is a method for enhancing contrast during imaging to assess cell and nuclear morphology of a sample. Between about 1% and about 10% by volume of acetic acid is applied to the sample. The sample is analyzed with an imaging device to create image data, the sample is diagnosed with the image data. As used herein, "image data" is to be read broadly to mean any data gathered by the imaging device. The use of the word "image" is not meant to connote a graphical representation—rather, by "image" and "imaging", it is meant any information relating to the sample gathered by one or more devices. Image data may be a string of numbers, a graphical representation, or any other data known in the art.

In other respects, the method includes applying between about 3% and about 10% by volume of acetic acid to the sample. The imaging device may include a confocal microscope. The imaging device may include an optical coherence tomography apparatus. The imaging device may include a photon migration imaging device. The imaging device may include a two-photon excited fluorescence imaging device. The imaging device may include a spectroscopy apparatus. The spectroscopy may include reflectance spectroscopy. The spectroscopy may include absorption spectroscopy. The spectroscopy may include fluorescence spectroscopy. The spectroscopy may include Raman spectroscopy. The sample may be in vitro. The sample may be in vivo.

In another respect, the invention is a method for enhancing contrast during imaging to assess cell and nuclear morphology of a sample, wherein between about 0.5% and about 10% by volume of Toluidine blue is applied to the sample. The sample is analyzed with an imaging device to create image data, and the sample is diagnosed with the image data.

In another respect, the invention is a method for enhancing contrast during imaging to enhance edges of cells of a sample. Between about 2 to about 10 times physiological concentrations of hypertonic saline is applied to the sample. The sample is analyzed with an imaging device to create image data, and the sample is diagnosed with the image data.

In another respect, the invention is a method for enhancing contrast during imaging to enhance edges of cells of a sample, wherein between about 0.1 to about 0.5 times physiological concentrations of hypotonic saline is applied to the sample. The sample is analyzed with an imaging device to create image data, and the sample is diagnosed with the image data.

In another respect, the invention is a method for enhancing contrast during imaging to assess cell and nuclear morphology of a sample, wherein between about 5% and about 10% by volume of Lugol's iodine is applied to the sample. The sample is analyzed with an imaging device to create image data, and the sample is diagnosed with the image data.

In another respect, the invention is a method for enhancing contrast during imaging to assess cell and nuclear morphology of a sample, wherein an absorbing dye is applied to the sample. The sample is analyzed with an imaging device to create image data, and the sample is diagnosed with the image data.

In other respects, the absorbing dye may include phycoerythrin. The absorbing dye may include indocyanine green. The absorbing dye may include lutetium texaphyrin. The analysis of the sample with an imaging device may include applying two or more illumination wavelengths to the sample, the scattering of the sample at the two illumination wavelengths being substantially different, analyzing the sample with an optical coherence tomography device to create image data, and diagnosing the sample with the image data.

In another respect, the invention is a method for enhancing contrast during imaging to assess cell and nuclear morphology of a sample, wherein a liposome is applied to the sample, the liposome containing a fluid of different refractive index. The sample is analyzed with an imaging device to create image data, and the sample is diagnosed with the image data.

In other respects, the fluid may include water. The fluid may include bovine serum albumin.

In another respect, the invention is a method for enhancing contrast during imaging to assess cell and nuclear morphology of a sample, wherein a contrast agent linked to a marker is applied to the sample. The sample is analyzed with an imaging device to create image data, and the sample is diagnosed with the image data.

In other respects, the marker may include CA125. The marker may include EGFR. The marker may include Her-2. The marker may include Annexin-V. The marker may include proliferating cellular nuclear antigen (PCNA). The marker may include endothelial growth factor receptor (EGFR). The marker may include vascular endothelial growth factor (VEGF). The marker may include human milkfat protein. The marker may include folate receptor.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A and 1B show confocal images ($\lambda$=808 nm) of SiHa cervical cancer cell before (FIG. 1A) and after (FIG. 1B) application of 6% acetic acid.

FIGS. 2A and 2B show an analysis of an acetic acid treated biopsy. Reflected light confocal images 50 $\mu$m below the epithelial surface (FIG. 2A) and 200 $\mu$m below the epithelial surface (FIG. 2B). Illumination wavelength was 808 nm.

DESCRIPTION OF ILLUSTRATIVE EMBODIMENTS

Figure 3A:
FIGS. 3A–3D show images of normal cervical biopsy before (FIG. 3A) and after (FIG. 3B) application of 6% acetic acid. Also shown are images of colposcopically abnormal cervical biopsy before (FIG. 3C) and after (FIG. 3D) addition of 6% acetic acid.
Figure 3B:
Figure 3C:
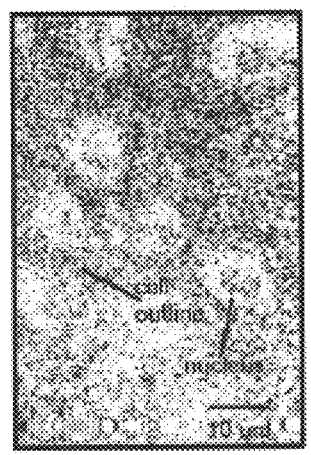
Figure 3D:
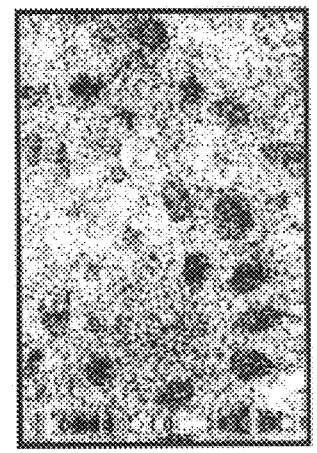
Figure 4A:
FIGS. 4A and 4B show confocal images of a cervical tissue slice after addition of 6% acetic acid (FIG. 4A). A corresponding hematoxylin and eosin (H&E) stained histologic section is also shown (FIG. 4B).
Figure 4B:
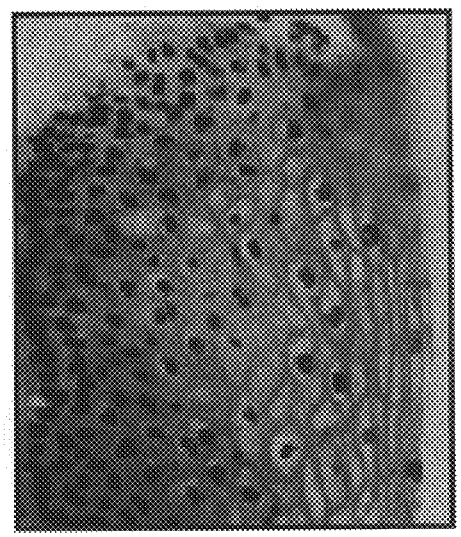
Figure 5A:
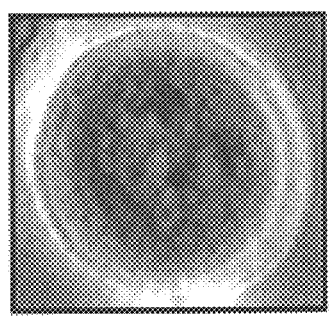
FIGS. 5A and 5B show a phase contrast image of epithelial cell before (FIG. 5A) and after (FIG. 5B) addition of 3% acetic acid.
Figure 5B:
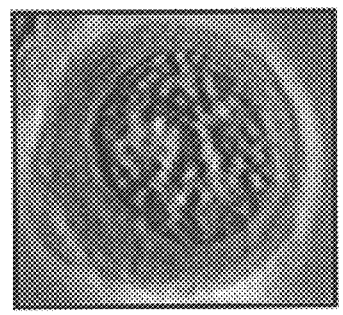

Pending U.S. patent application Ser. No. 09/272,719, filed Mar. 19, 1999 and entitled "Fiber-Optic Confocal Imaging Apparatus and Methods of Use" is hereby incorporated by reference in its entirety. Pending U.S. patent application Ser. No. 09/303,278, filed Apr. 30, 1999 and entitled "Method and Apparatus for Subsurface Imaging" is hereby incorporated by reference in its entirety. Pending U.S. patent application Ser. No. 09/175,234, filed Oct. 20, 1998 and entitled "Acetic Acid as a Contrast Agent in Reflectance Confocal Imaging of Tissue" is hereby incorporated by reference in its entirety.

Certain extrinsic contrast agents have been used in the clinical setting to aid in the visual differentiation between normal and abnormal tissue. Disclosed herein are important extensions of this general method, having specific applications, at least, in the early detection of microinvasive disease. Clinically relevant in itself, the progression of cervical cancer is believed to be typical of other types of epithelial cancer, including those of the oral cavity, larynx, colon and ovaries, all of which are serious health concerns. Demonstration of the feasibility of use of contrast agents for the early detection of malignancy may enhance the ability to better treat all of these diseases. Coupling that to the availability of instruments capable of real time imaging provides a powerful tool capable of detecting disease earlier so that it may be more successful.

Extrinsic contrast agents are capable of changing the scattering properties of cells and tissues enough to be measured by instruments such as confocal microscopy and OCT. Clinical evidence has shown that there are differential effects of these contrast agents in normal, pre-cancerous and cancerous tissue, with diagnostic potential. Acetic acid and toluidine blue may give rise to increased backscatter from diseased areas, and Lugol's iodine solution may result in increased backscatter from the normal areas of tissue. The effects of hypertonic saline solution may be similar to those of acetic acid and toluidine blue, increasing backscatter from cancer cells more than normal cells.

Different optical imaging techniques may rely upon the addition of exogenous agents to enhance intrinsic contrast. Specifically, acetic acid and hypertonic saline may be used as contrast agents to enhance contrast between different types of samples, such as normal and diseased cells, including normal and diseased cells in regions of the cervix. Without being bound by theory, it is believed that application of such agents may result in changes in the refractive index of cells. Without being bound by theory, it is believed that acetic acid and possibly other agents may cause crosslinking of nuclear proteins, resulting in heightened refractive index fluctuations in the nucleus, and increasing nuclear backscattering. Without being bound by theory, it is believed that hypertonic saline and other agents may induce osmotic stress, causing changes in the size and index of refraction of various cell components, which may beneficially affect image contrast.

Figure 6:
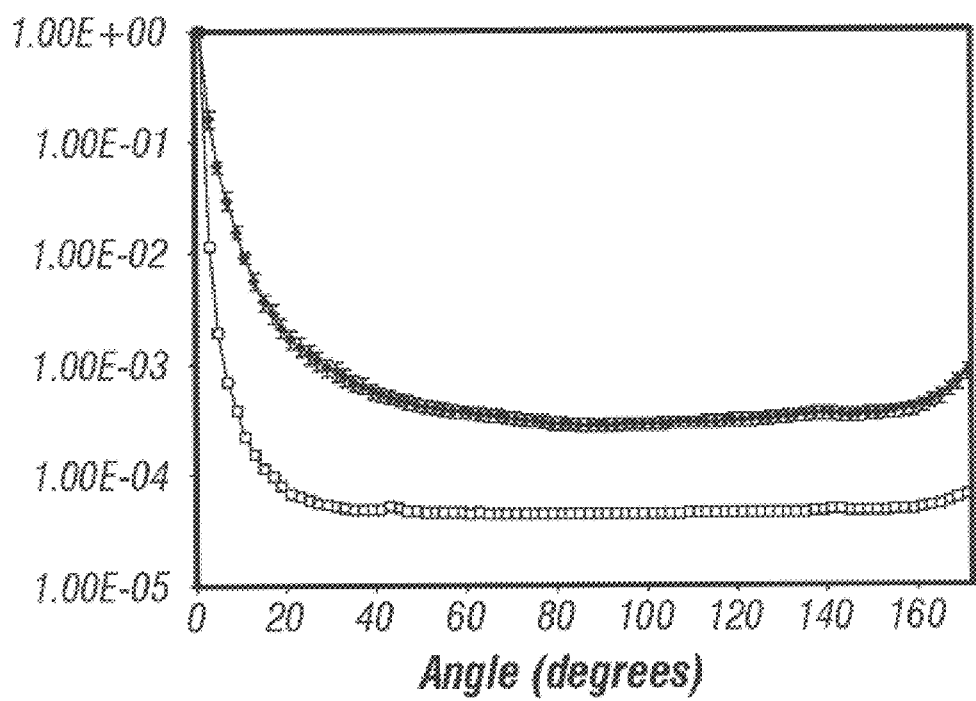
FIG. 6 shows phase functions of OVCA420 cells before (bottom line) and after (top line) addition of 3% acetic acid.
Figure 7A:
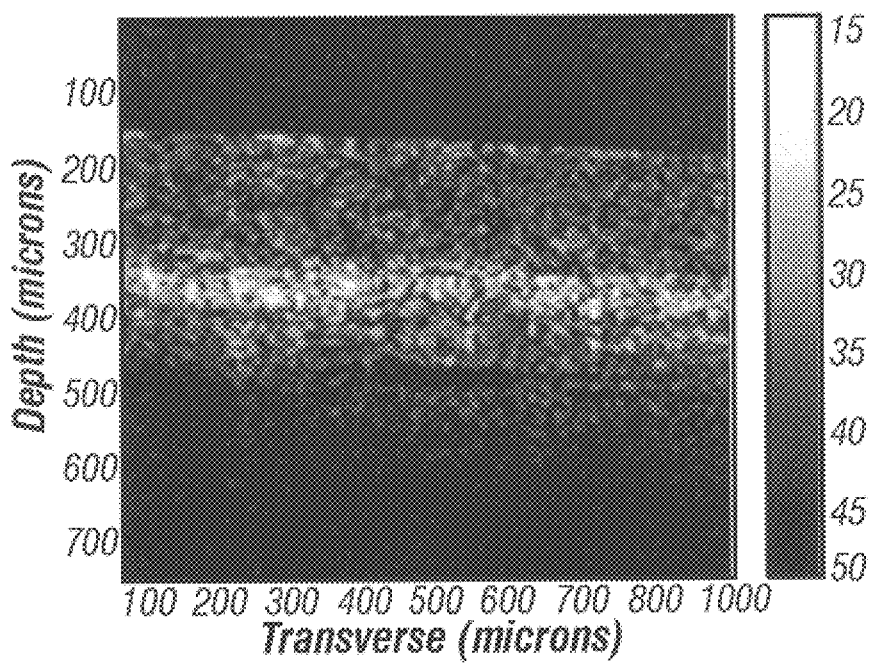
FIGS. 7A and 7B show OCT in-vivo images of normal human buccal mucosa before (FIG. 7A) and after (FIG. 7B) the application of acetic acid.
Figure 7B:
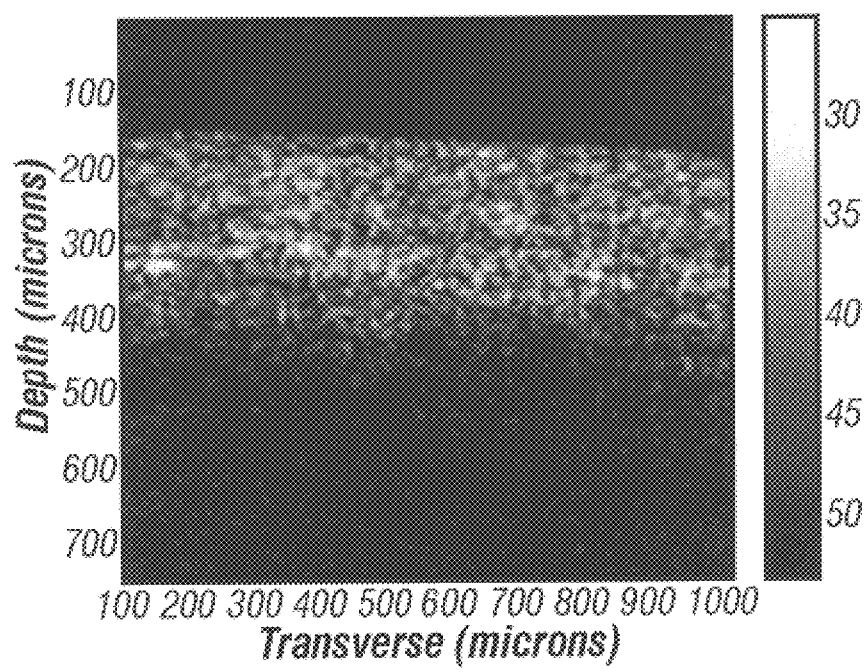

FIGS. 1–7 demonstrate the contrast-enhancing effects of contrast agents according to the present disclosure. Turning first to FIGS. 1A and 1B, there is shown confocal images ($\lambda$=808 nm) of a SiHa cervical cancer cell. FIG. 1A shows the cell before application of a contrast agent, while FIG. 1B shows the cell after the application of 6% acetic acid. FIGS. 2A and 2B show an analysis of an acetic acid treated biopsy. A reflected light confocal image ($\lambda$=808 nm) 50 $\mu$m below the epithelial surface is shown in FIG. 2A, and a reflected light confocal image ($\lambda$=808 nm) 200 $\mu$m below the epithelial surface is shown in FIG. 2B. FIGS. 3A and 3B show images of normal cervical biopsy before (FIG. 3A) and after (FIG. 3B) application of 6% acetic acid. FIGS. 3C and 3D show images of colposcopically abnormal cervical biopsy before (FIG. 3C) and after (FIG. 3D) addition of 6% acetic acid. FIGS. 4A and 4B show confocal images of a cervical tissue slice after addition of 6% acetic acid (FIG. 4A). A corresponding hematoxylin and eosin (H&E) stained histologic section is shown in FIG. 4B. FIGS. 5A and 5B show a phase contrast image of epithelial cell before (FIG. 5A) and after (FIG. 5B) addition of 3% acetic acid. FIG. 6 shows phase functions of OVCA420 cells before (bottom line) and after (top line) addition of 3% acetic acid. FIGS. 7A and 7B show OCT in-vivo images of normal human buccal mucosa before (FIG. 7A) and after (FIG. 7B) the application of acetic acid.

Contrast agents traditionally viewed as absorbers may also be used in scattering-based imaging modalities such as, but not limited to, confocal microscopy. Absorbers may be used because absorption is directly related to the imaginary component of the refractive index that, in turn, may be related to the real component of the refractive index through Kramers-Kronig integration. Very high local absorption is needed for this, in the order of $10^4$ cm$^{-1}$ for a change in relative index of refraction of 0.05~0.1. Changes in refractive index may alter the scattering properties of the cells which may affect image contrast. Without being bound by theory, it appears that Toluidine blue and Lugol's iodine may be two such agents. These agents may have diagnostic utility for viewing, for instance, suspected dysplastic regions in the cervix and oral cavity.

Contrast agents linked to markers associated with ovarian cancer, which increase the local index of refraction, may also be utilized to improve biomedical imaging. Liposomes are membrane-bound spherical structures that may be linked to antibodies to cell surface antigens. Liposome based systems may selectively increase the backscattering of neoplastic ovarian cells to produce enhanced contrast in images, such as OCT images. Without being bound by theory, liposomes, which are small compared to an illumination wavelength and which contain a high index fluid, may produce the greatest increase in backscattering.

Figure 8:
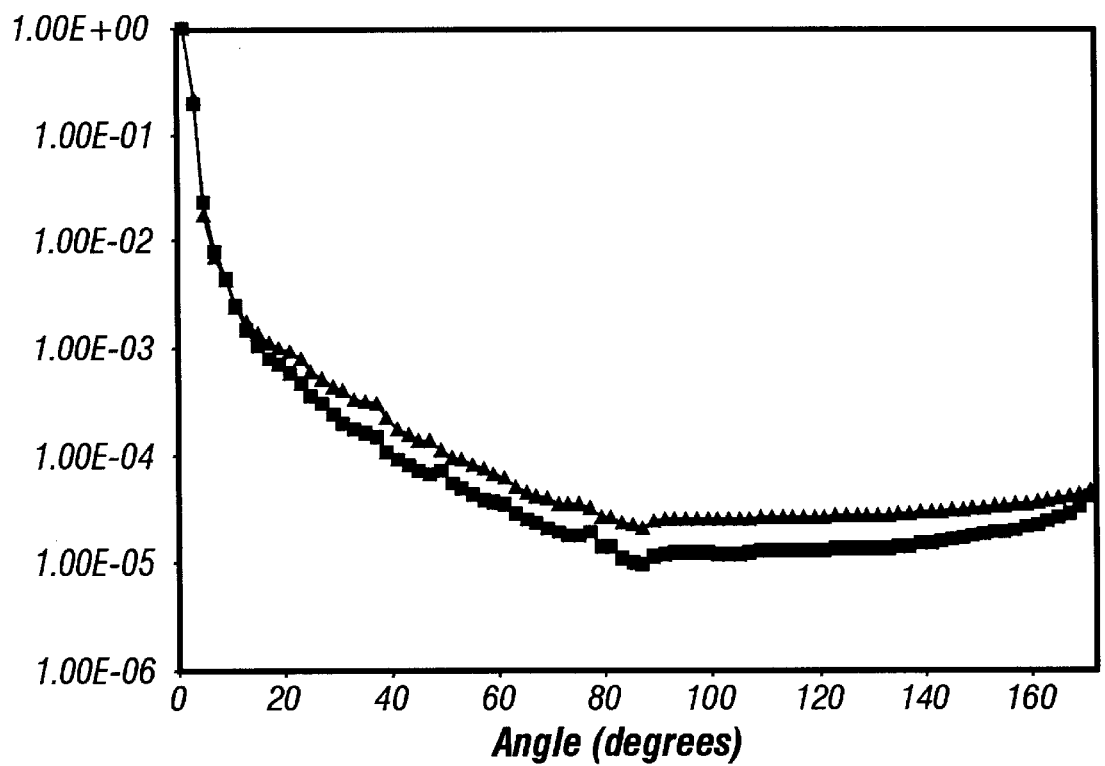
FIG. 8 shows measured scattering phase function of 18 $\mu$m diameter polystyrene microspheres before (bottom line) and after (top line) tagging with 250 nm diameter liposomes.

To demonstrate this technique, 250 nm diameter liposomes filled with water were attached to 18 $\mu$m diameter polystyrene microspheres. Scattering phase functions were measured before and after attachment of liposomes; liposomes produced an increase in backscattering as shown in FIG. 8. Specifically, FIG. 8 shows a measured scattering phase function of 18 $\mu$m diameter polystyrene microspheres before (bottom line) and after (top line) tagging with 250 nm diameter liposomes. More significant increases may be made by increasing the index of the fluid within the liposomes (for example, by adding bovine serum albumin (BSA), this index may be increased up to 1.43). Routine simulations and studies may be conducted to determine the ideal size, index and marker for liposomes enhanced contrast in different imaging techniques such as OCT, beginning with polystyrene spheres, moving to cells suspensions, then RAFT cultures and finally in vitro ovarian tissue. Markers that may be useful include but are not limited to CA125 ($10^6$/cancer cell, $10^0$/normal cell), EGFR ($10^{4-5}$/cancer cell, $10^4$/normal cell) and Her-2 ($10^{4-6}$/cancer cell, $10^4$/normal cell), PCNA, EGFR, VEGF, human milkfat protein, and folate receptor.

Increased backscattering may also be achieved by adding strongly absorbing extrinsic dyes which accumulate selectively in neoplastic ovarian cells. An increase in local absorption coefficient leads to an increase in refractive index and backscattering. This approach to increased backscattering is designed to mimic the backscattering of melanin. The intrinsic absorber melanin is present in melanosomes which are small compared to the incident wavelength. Melanin granules produce very strong backscattering which can clearly be observed in OCT and confocal images of skin. Although melanin is strongly absorbing, because it is present in such small packages, the total absorption cross section is low. However, images may be obtained deep within melanotic tissues by taking advantage of its backscattering.

The Kramers Kronig integral provides a direct relationship between the wavelength dependent real and imaginary parts of the refractive index and may be used to predict how much of an increase in local absorption is required to produce a significant change in the refractive index. Calculations show that for a 10 nm wide absorption band, a local absorption coefficient of $10^4$ cm$^{-1}$ is required to produce an increase of 0.05 in refractive index. Although most biological absorbers do not produce such high absorption in tissue (melanin is an exception), there are many extrinsic dyes (such as phycoerytarin) with extinction coefficients exceeding $10^6$ cm$^-$M$^{-1}$ so that the needed absorption may be achieved at local dye concentrations of several hundred $\mu$M. Absorbing dyes which localize in membranes so that structures small compared to the wavelength such as mitochondria will accumulate the absorber and produce backscattering may also be utilized. The increase in local absorption may be measured using an absorption microspectrophotometer.

The use of wavelength-ratiometric OCT (WROCT) to produce high contrast images of ovarian cancer using the absorption of extrinsic chromophores may also be utilized. The absorption differences produced by extrinsic chromophores linked to antibodies for markers associated with ovarian cancer may be used. Here, only relatively small changes in the absorption coefficient—less than 1 cm$^{-1}$ need to be produced. Dyes developed for photodynamic therapy with NIR illumination present an excellent choice for this approach, since they absorb in the NIR and accumulate preferentially in neoplastic tissues. A variety of such dyes may be used. For instance, indocyanine green (FDA Approved) and lutetium texaphyrin may be used first in cell cultures to determine the expected differential absorption, then in RAFT cultures, and finally in in vitro ovary. With both dyes, preferential accumulation leading to a tenfold increase in drug concentration has been reported in tumors, resulting in increased absorption at 740 (texaphyrin) and 760 nm (ICG).

The beneficial contrast-enhancing effects of acetic acid, toluidine blue, Lugol's iodine and hypertonic saline solution on human cultured cells may be analyzed using live, human normal (for instance, Clonetics CrEC-Ec-ectocervical cervical epithelial) and human neoplastic (for instance, HeLa and SiHa lines) cervical epithelial cells. The cells may be exposed to different contrast agents while in growth medium and then studied under, for example, brightfield, phase and reflected light confocal microscopy. Brightfield and phase microscopy images may be used to gain qualitative insight as to what specific parts of the cell are most affected by each of the contrast agents. Reflected light-confocal microscopy images may be used to assess changes in back-reflectance induced by each of the contrast agents, comparing it to the qualitative structural information obtained via light and phase microscopy. Confocal images may be obtained at 808 nm, the available wavelength closest to the 855 nm center wavelength at which a typical OCT system operates. However, with the benefit of the present disclosure, those of skill in the art will understand that other illumination wavelengths may be used.

Although certain contrast enhancing techniques discussed above generally relate to the preparation and topical application of contrast agent(s) to a sample that may, for example, affect the backscattering of normal and neoplastic cells differently, the present disclosure additionally encompasses contrast-enhancing techniques relating to the use of wavelength itself as a contrast mechanism. Specifically, the selection of wavelengths where the backscattering and/or absorption of, for instance, normal and neoplastic cells differ most may itself be used to enhance contrast in biological imaging applications. More specifically, selection of wavelength in OCT and spectroscopy applications may benefit from a resultant increase in contrast between normal and neoplastic cells through the selection of an appropriate contrast-enhancing wavelength or wavelengths.

In mapping absorption using wavelength-ratiometric OCT (WROCT), it is known that two illumination wavelengths may be selected where the scattering cross section is similar. If, however, two wavelengths are chosen where the scattering of a particular structure is different, but the absorption is similar, WROCT images may enhance the contrast associated with that structure. Thus, wavelength dependence of backscattering may be exploited to enhance contrast in OCT images. As the wavelength is increased, the backscattering increases. Appropriate models known in the art may be used to predict whether the wavelength dependence of backscattering differs significantly for normal and neoplastic ovarian cells and if so, to determine which wavelengths may be optimal to recognize particular ovarian cancer cells. The technological development of WROCT may then be taken advantage of to add differential wavelength contrast to images of anatomic microstructure. This method may be applied to a vast array of different samples, including but not limited to, cell cultures, RAFT cultures, in vitro ovary and in vivo.

Integration of spectroscopic information may provide another dimension to increase contrast. Building on recent advances using Fourier-domain reconstruction of OCT ranging data, a fiber optic probe may be developed which has no moving parts to simultaneously record the spectrum of fluorescent light emitted from the surface of a tissue site and to record the subsurface structure with high spatial resolution using OCT.

Apart from being able to obtain 2 or 3-D OCT images without moving parts, a system may be built that allows for the addition of functional elements, or modules that may perform other measurements, including, for instance, simultaneous optical measurements. For example, a multi-wavelength fluorescence module may be incorporated with an OCT device. The module may use the same delivery and collection optics as the OCT device, but it may separate its signal band by the use of a dichroic mirror. This setup allows for simultaneous measurement of an OCT image together with the spectrally and spatially resolved fluorescence at each point along the surface of the OCT image. In a similar fashion, other modules may be incorporated to allow for, for example, the visual monitoring of a surface being measured; measurement of full field surface fluorescence; and for delivery of therapeutic optical radiation. All of these may be implemeited while monitoring the sub-surface structure with, for instance, Fourier domain OCT.

Using such a system, the fluorescence of intrinsic chromophores may be utilized. Further, additional contrast provided by extrinsic fluorophores may be utilized. Fluorophores may be linked to antibodies to CA125 receptors, EGFR receptors and Her-2 receptors. Further, TRITC may be used as a fluorophore because of its high quantum yield and red excitation which may allow for deep penetration.

OC125, antibody to CA125, has been linked to fluorophore in at least one laboratory and may be utilized for contrast. This may either be added to a cell culture or painted on an ovary and may be a marker for expression of CA125. Specifically, OC125 (the antibody to CA125) may be linked to the TRICT fluorophore. Ovaries may be painted with a solution containing the fluorophore labeled OC125 and washed after 30 minutes. Such ovaries may be imaged and may exhibit beneficially-enhanced contrast.

Probes may be used to study the properties of normal ovarian cells, transformed cells and ovarian cancer cells grown in monolayer. OC125 linked to a fluorophore may be used to determine the amount of CA125 expression in this population. Normal ovarian surface epithelium lacks CA125 expression along with SV40 T antigen immortalized epithelial cells. Transfected cells which are known to express CA125 may be used as controls for the CA125 linked antibody. Anti-Her-2 (TA1 antibody) antibody and anti-EGFR antibody (225 antibody) may also be utilized to develop other markers for underlying pathology.

Annexin-V linked to fluorophore may be used to assess apoptosis. Phosphatidyl serine is translocated from the inner plasma membrane to the outer plasma membrane early in apoptosis. Annexin-V has a high binding affinity for phosphatidyl serine and is easily linked to a fluorophore. This may be an accurate and easy method of assessing apoptosis and may therefore be utilized as a marker for intrinsic activity on an ovarian surface.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Topical Contrast Agents

Light, phase and confocal microscopy images have been obtained from samples from a cervical cancer cell line (SiHa) to demonstrate the changes in the scattering properties resulting from the addition of certain contrast agents. Brightfield and phase microscopy provide information on the areas or structures in the cells affected by the contrast agent being used. Reflected light confocal microscopy was then used to evaluate how the changes in the cells altered their backscattering characteristics at wavelengths of 514.5 and 780 nm. The results are summarized in FIG. 9.

To determine the effect of contrast agents on the backscattering properties of the studied cells, samples in growth medium were exposed to the different contrast agents. The cell samples consisted of 20 µl of cell suspension of concentration $10^6$ cells/ml. The concentrations of the contrast agents are shown in the following table, although with benefit of the present disclosure those having skill in the art will recognize that other concentrations suitable for enhancing contrast may be substituted therewith. For example, in one embodiment, a range of about 1% to about 10% of acetic acid (and, in another embodiment between about 3% and about 6%) is contemplated, a range of about 0.5% to about 10% Toluidine blue is contemplated, a range between about 2 to about 10 times physiological concentrations (which, may, in one embodiment be about 140 millimolar) Hypertonic saline is contemplated, a range between about 0.1 to about 0.5 times physiological concentrations Hypotonic saline is contemplated and a range of about 5% to about 10% Lugol's iodine is contemplated. With the benefit of the present disclosure, however, those having skill in the art will recognize that several other concentration ranges may be utilized according to the present invention to enhance contrast in biological imaging.

| CONTRAST AGENT | PREPARATION |
| --- | --- |
| Acetic acid | 6% (volume) glacial acetic acid in deionized water |
| Toluidine blue | 1% (weight) toluidine blue O dye in deionized water |
| Hypertonic saline | 840 mM phosphate buffered saline (6× physiologic concentration) |
| Lugol's iodine | 5% iodine and 10% potassium iodine in deionized water |

The cells were kept in the growth medium to maximize their viability. However, this meant that the amount of contrast agent needed to observe an effect varied from sample to sample. In all cases, contrast agent was added to effect, although never exceeding a 1:1 dilution of the cell solution. The cells were then examined under brightfield and phase microscopy, and under reflected light confocal microscopy at 514.5 and 808 nm.

Figure 9:
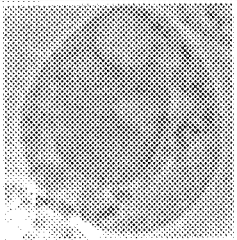
FIG. 9 shows effects of contrast agents on the backscattering properties of human neoplastic, cervical epithelial cells. The "Native" row contains no contrast agent; the "Acetic acid" row contains 6% by volume; the "Toluidine blue" row contains 1% by weight; the "Hypertonic saline" row contains 6x physiologic concentration; the "Lugol's iodine" row contains 5% iodine and 10% potassium iodine. The first column shows phase contrast (brightfield for Lugol's Iodine and Toluidine blue) pictures of cells. The center and right columns show reflected light confocal images at 514.5 and 808 nm respectively.

FIG. 9 shows the results of adding different contrast agents to human neoplastic, cervical epithelial cells. N stands for native, in their growth medium; AA indicates addition of acetic acid; TB denotes the addition of toluidine blue; HS indicates the addition of hypertonic saline solution; and LI the addition of Lugol's iodine solution. The first column shows phase contrast images of the cells (brightfield for LI). The central and right columns show reflected light confocal images at 514.5 and 808 nm, respectively. The laser power was kept to within 10% of a set level for each set of confocal measurements. The resulting images were then post-processed by adjusting brightness and contrast. Post processing was the same for all of the images at a given wavelength.

The first row of FIG. 9 shows the cells in their growth medium. The phase picture shows a typical cell. The nucleus is clearly defined, as well as an assortment of organelles in the cytoplasm. The confocal images show cells that, although well-defined in the periphery, do not show the intra-cellular detail that the phase contrast picture shows. It is also worth noting the lower resolution of the image obtained at the longer wavelength. The second row shows the effect of the addition of acetic acid to the cells. Without being bound by theory, acetic acid is hypothesized to cross-link the protein inside the cell, effectively coagulating it. The phase contrast image shows a change especially in the nucleus, which is now more distinct from the cytoplasm.

With reference again to FIG. 9, confocal images of the addition of acetic acid show a similar effect. The whole cell is brighter with the nucleus standing out. The addition of toluidine blue is shown in the next line. Although the dye is absorbed throughout the cell, making it look darker in the phase contrast image, it is seen to concentrate especially in the nucleus. The confocal images show increased visualization of the nucleus without significantly increasing backscattering from the cytoplasm. This results in increased contrast between the nucleus and cytoplasm relative to the acetic acid image. The addition of hypertonic saline solution to the cells had an interesting effect, resulting in the relocation of the organelles to the edges of the cell. This result is seen especially well in the 514.5 nm confocal image, which shows a well defined nucleus inside a cell with a clearly defined outline and a void between the cell wall and the nucleus. This is in contrast to the homogeneous appearance of the whole cell in its native state. Assuming the mechanism for the change in scattering is similar to that observed with toluidine blue, addition of Lugol's iodine may result in increased backscatter from normal cells. The brightfield image shows that the dye was absorbed evenly throughout the cell. This results in a negligible change in the confocal images, which show homogeneous backscatter from the entire cell as in the native case.

All of the compositions and/or methods and/or apparatus disclosed and claimed herein may be made and executed without undue experimentation in light of the present disclosure. While the compositions and methods of this invention have been described in terms of specific embodiments, it will be apparent to those of skill in the art that variations may be applied to the compositions and/or methods and/or apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 2

Normal and malignant human cervical cancer cells were imaged in vivo with confocal, phase contrast and brightfield microscopies. Results were compared between cells in growth medium before and after addition of acetic acid, hypertonic saline solution, toluidine blue and Lugol's iodine.

Two types of human cervical cells were used in this study: normal cells from primary culture and an immortalized cancer cell line (SiHa line). The cells were imaged with confocal microscopy in growth medium and after the addition of four contrast agents: acetic acid, hypertonic saline, toluidine blue and Lugol's iodine. The following contrast agents were used:

| CONTRAST AGENT | PREPARATION |
| --- | --- |
| Acetic acid | 6% (volume) glacial acetic acid in deionized water |
| Toluidine blue | 1% (weight) toluidine blue O dye in deionized water |
| Hypertonic saline | 840 mM phosphate buffered saline (6× physiologic concentration) |
| Lugol's iodine | 5% iodine and 10% potassium iodine in deionized water |

As previously stated, with benefit of the present disclosure those having skill in the art will recognize that other concentrations suitable for enhancing contrast may be substituted therewith. The cells were also imaged using phase contrast and transmitted light microscopy. Phase contrast microscopy was used to image cells before and after addition of acetic acid and hypertonic saline solution. Cells were imaged under transmitted light before and after the addition of toluidine blue and Lugol's iodine solution.

Normal and malignant human cervical epithelial cells were obtained. The cervical carcinoma cells (SiHa line) were obtained from the American Type Culture Collection (Rockville, Md.). This cell line is HPV-16 (Human Papillomavirus-16) positive. SiHa cells were cultured in D-MEM (Dulbecco's modified eagle media) growth medium and Ham's F12 (GIBCO, Grand Island, N.Y.) with supplements of 5% (vol/vol) fetal bovine serum (GIBCO) and antibiotics (100 Units/mL penicillin and 100 mg/mL streptomycin). The normal cells were purchased from Clonetics (Walkersville, Md.) and cultured through one passage in keratinocyte growth medium-2 (Clonetics). Routine checks for mycoplasma ensured that the cell cultures were free of contamination. After brief incubation with 2 mM ethylenediamine-tetraacetic acid and 0.25% trypsin, the cultures were dispersed by repeated pipeting.

Four different samples of SiHa cells were obtained and imaged on four different days. A single sample of normal cells from one culture was obtained and imaged on a fifth day. Each day, images of available cells were obtained before and after the addition of each contrast agent. For confocal measurements, cell suspensions in growth medium were obtained in concentrations of $10^6$ cells per milliliter. 20 microliter aliquots were placed atop a layer of gelatin prepared in a Petri dish and imaged under a confocal microscope. The gelatin layer was used to reduce the specular reflectance from the bottom of the Petri dish, which may otherwise overwhelm the signal from the cells.

The cells were then exposed to the same volume (20 $\mu$l) of one of the contrast agents chosen; the process was repeated starting with a fresh aliquot of cells for each of the agents. Identical methodology was followed for brightfield and phase contrast imaging of the cells, with the exception that the cell and contrast agent aliquots were placed on glass microscope slides.

Confocal images were obtained using a laser scanning confocal microscope at a wavelength of 808 nm. The field of view could be varied between 54×54 $\mu$m and 330×330 $\mu$m with a maximum lateral resolution of 0.8 $\mu$m. The depth resolution of the system was 2 $\mu$m. Images were obtained at 15 frames per second. After acquisition, the images were converted to 8-bit grayscale values. Value 0 (black) corresponds to lowest reflectance and value 255 (white) corresponds to highest reflectance.

An estimate of the grayscale offset of the images was obtained after visual examination of all image histograms. Histogram stretching was used to enhance image contrast. For the images of normal cells, grayscale value 60 was reassigned to zero and grayscale values higher than 60 were evenly distributed along the entire 8-bit range (0–255). The images of the cancer cell line were similarly processed by shifting value 30 to zero and evenly distributing the higher values along the 8-bit range. These differences in the zero level of the confocal images were attributed to normal drift in instrument performance. All subsequent analysis was done on the adjusted confocal images.

The cells were also imaged using brightfield and phase contrast microscopy to establish correlations between features of the confocal images and cell morphology. Images were digitized in color using a CCD camera attached to the trinocular port of the microscope. The 24-bit, color images were converted to 8-bit grayscale images and were inverted before display. Thus, in the brightfield images, white corresponds to highest absorption (lowest transmission) and black to lowest absorption (highest transmission). All images were then appropriately adjusted to a common spatial scale.

Figure 10:
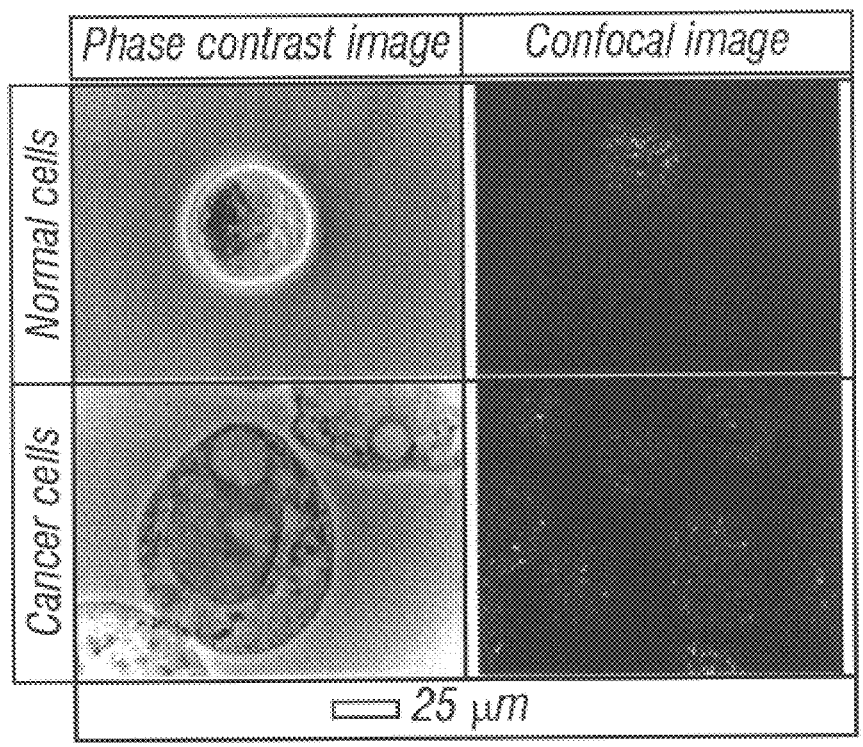
FIG. 10 shows the phase contrast and confocal images of normal and cancer cells in culture medium.

FIG. 10 shows confocal images of normal and cancer cells in growth medium. For comparison, the confocal images are shown alongside phase contrast images of the same cell sample. A scale bar 25 microns wide, common to FIGS. 10–14. The phase contrast images show the general morphology of the cells. The normal cell is round with an observed diameter of about 20 microns. The nucleus, the largest structure inside the cell, is seen as a dark structure about half the diameter of the cell, at the 10 o'clock position. Organelles are faintly observed in the cytoplasm. The cancer cells have a round shape, about 25 microns in diameter in this image. Inside the cell membrane, a large number of organelles are observed as dark spots of varied diameters, distributed throughout the cytoplasm. The largest structure inside the cell is the nucleus.

The confocal image of the normal cell shows a single round cell about 20 microns in diameter. The nucleus is very faintly visible as a brighter region at the 2 o'clock position. The image of the cancer cells shows five full and at least four partial cells. The cells are round in shape and have diameters around 20 microns. The nucleus is most apparent in the largest fully imaged cell (lower right) at the 1–2 o'clock position. Noticeable background noise is observed as a series of thin vertical lines. The confocal images show very dim cells, with poorly defined outlines and very low nuclear-to-cytoplasmic contrast. To quantify these differences, average grayscale values were determined for representative nuclear, cytoplasmic and background areas of images. Seven and ten cell images were sampled for the normal and cancer cell lines respectively. For the con focal image of the normal cells the average values for cytoplasmic and nuclear images were 44.7 and 67.4, over a background level of 18.2. For the cancer (SiHa line) cells, the corresponding values were 24.0 for the cytoplasm, (C) and 28.0 for the nucleus (N), and 5.1 for the background (B).

Figure 11:
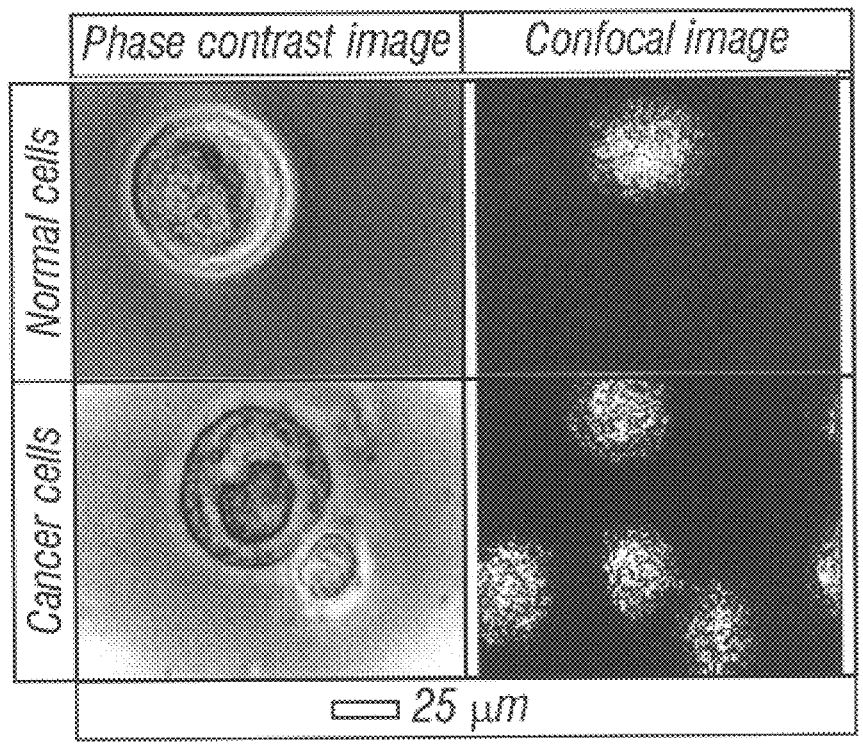
FIG. 11 shows the phase contrast and confocal images of normal and cancer cells after the addition of 6% acetic acid.

Phase contrast and confocal images of cells exposed to 6% acetic acid are shown in FIG. 11. The first row of images shows images of normal cells, and the second row shows images of cancer cells. The scale bar at the bottom, common to all images, is 25 microns wide. The phase contrast image of the normal cell exposed to acetic acid shows a round cell about 25 microns in diameter. The cell nucleus is seen as the single large structure inside the cell. One of the distinguishing features of this image, with respect to the phase contrast image of the cells in growth medium, is the relative texture of the visible cell components, especially the nucleus. After the addition of acetic acid the components appear to have a rougher look. The phase contrast images of cancer cells show similar effects, especially in the nucleus. No change in the distribution of organelles in the cytoplasm is apparent.

The confocal images after addition of acetic acid show a dramatic increase in the overall reflectance from the cells. The confocal image of the normal cell shows a cell about 25 microns in diameter with a much more apparent, brighter nuclear structure in the center 6 o'clock position of the cell. The nucleus appears to have a diameter two-thirds that of the cell, in good agreement with the corresponding phase contrast image. Like the normal cells, the cancer cells show greater overall scattering and nuclear differentiation in the confocal image. Almost four full cancer cells, all with similar characteristics, are seen in the image. The average grayscale values of five normal cells are: 64.6 (C) and 186.8 (N), with a background of 18.6. The values for ten cancer cells are 52.9 (C), 175.2 (N) and 5.1 (B).

Figure 12:
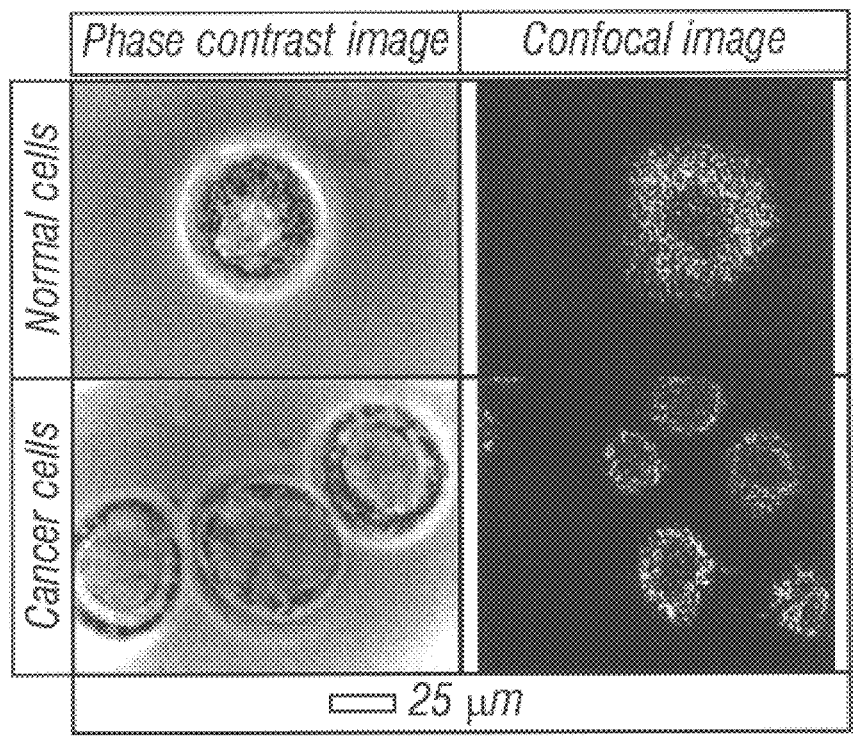
FIG. 12 shows the phase contrast and confocal images of normal and cancer cells after the addition of hypertonic saline solution.

Phase contrast and confocal images of cells exposed to hypertonic saline solution are shown in FIG. 12. The phase contrast images here show an interesting change in the distribution of organelles inside the cell. The phase contrast image of the normal cell shows that organelles have migrated to the edge of the cell, leaving a lighter, more uniform void in the center probably containing the nucleus. In the phase contrast image of the cancer cells, almost all of the small organelles have moved toward the cell membrane. No other changes are observed in the nuclei or overall cell structure. The shapes and sizes of the cells and their nuclei are similar to those observed in the cells in growth medium alone.

The confocal images of the cells exposed to hypertonic saline solution show increased overall scattering and outline differentiation. They show higher nuclear-to-cytoplasmic contrast, but in these images nuclei appear darker than the surrounding cytoplasm. The average grayscale values for these images are: 84.74 (C), 50.45 (N), and 8.88 (B) for five normal cells; and 90.05 (C), 46.14 (N), and 4.82 (B) for ten cancer cells.

Figure 13:
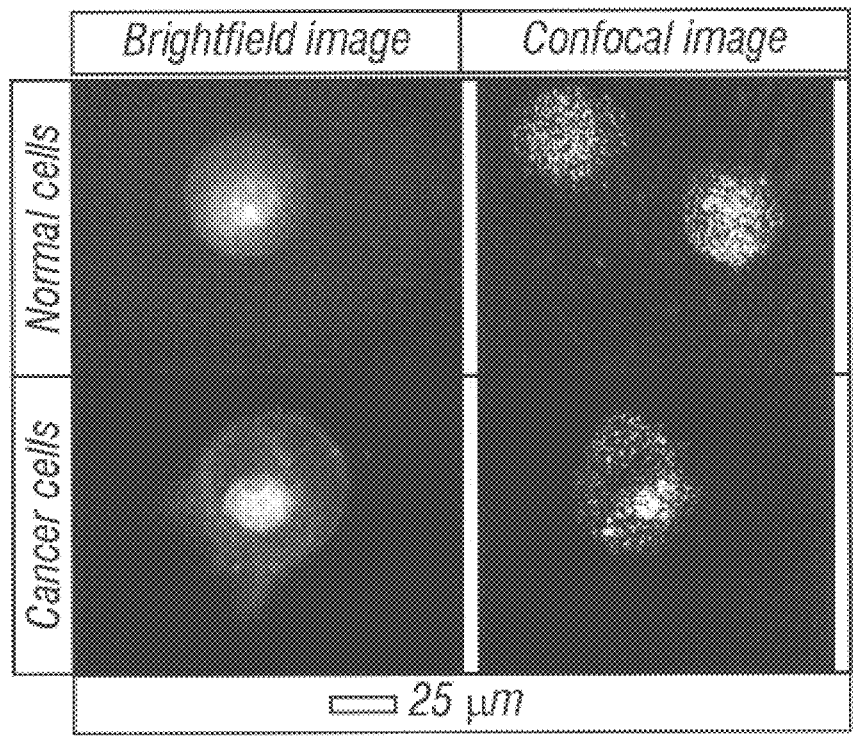
FIG. 13 shows Brightfield and confocal images of normal and cancer cells after the addition of 1% toluidine blue solution.

FIG. 13 shows brightfield and confocal images of the normal and cancer cells after the addition of 1% toluidine blue solution. The inverted brightfield images show that the solution permeates the whole cell, although it concentrates in the nucleus. This is shown by the brighter regions of the image, which correspond to higher absorption. The cytoplasmic region of the normal cell shows relative uniformity in the measured absorption. The uptake of solution in the nucleus appears more uneven, with appreciable hot spots. Toluidine blue uptake in the cytoplasm of the cancer cell is not as uniform and appears to be slightly higher in the cell membrane and several filament-like regions inside the cytoplasm. The nucleus also exhibits bright spots. No morphologic changes were evident in any of the cells.

The confocal images of cells after the addition of toluidine blue show higher overall scattering and increased nuclear-to-cytoplasmic contrast. This is illustrated in the image of the normal cells, although the differentiation of nucleus and cytoplasm is not as high as in the cancer cells. In the image of the cancer cell, the nuclear region is located at the 4 o'clock position, and the differentiation is most evident. This image shows average grayscale values of 25.79 (C), 93.45 (N), and 5.13 (B) for 10 images. The corresponding values for five images of the normal cell are 57.47 (C), 138.27 (N) and 21.14 (B).

Figure 14:
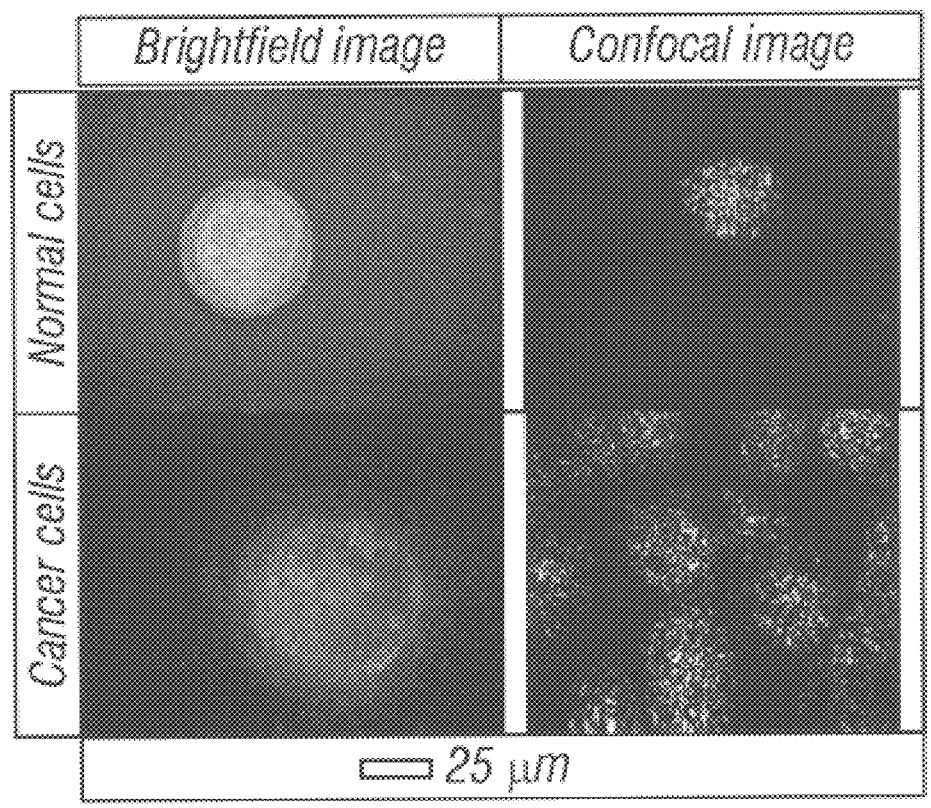
FIG. 14 shows Brightfield and confocal images of normal and cancer cells after the addition of Lugol's iodine solution.

FIG. 14 illustrates brightfield and confocal images of normal and cancer cells after the addition of Lugol's iodine. The inverted, brightfield images show regions of higher solution uptake in lighter shades of gray. The image of a normal cell shows a round cell about 20 microns in diameter with relatively uniform uptake of Lugol's iodine solution throughout the cell. The nucleus is distinguishable in the center of the cell and appears slightly brighter than the cytoplasm, especially around the edges. The brightfield image of the cancer cell shows slight uptake of the solution. Absorption is uniform throughout the cytoplasmic region of the cell and slightly lower in the nuclear region. This cell is also round in shape and 25 microns in diameter.

The confocal images of the cells show greater scattering than those of the cells in growth medium alone, giving better outline definition. However, the treated cells show little increase in the differentiation of intracellular structures. Both the normal and cancer cells appear of fairly uniform brightness. A structure, probably nuclear, is represented by slightly increased backscatter in the confocal image of the normal cell at the 7 o'clock position. The average intensity values for these images are: 80.26 (C), 144.67 (N) and 17.53 (B) for five confocal images of normal cells; and 50.18 (C), 95.33 (N) and 8.98 (B) for 10 images of cancer cells.

Figure 15A:
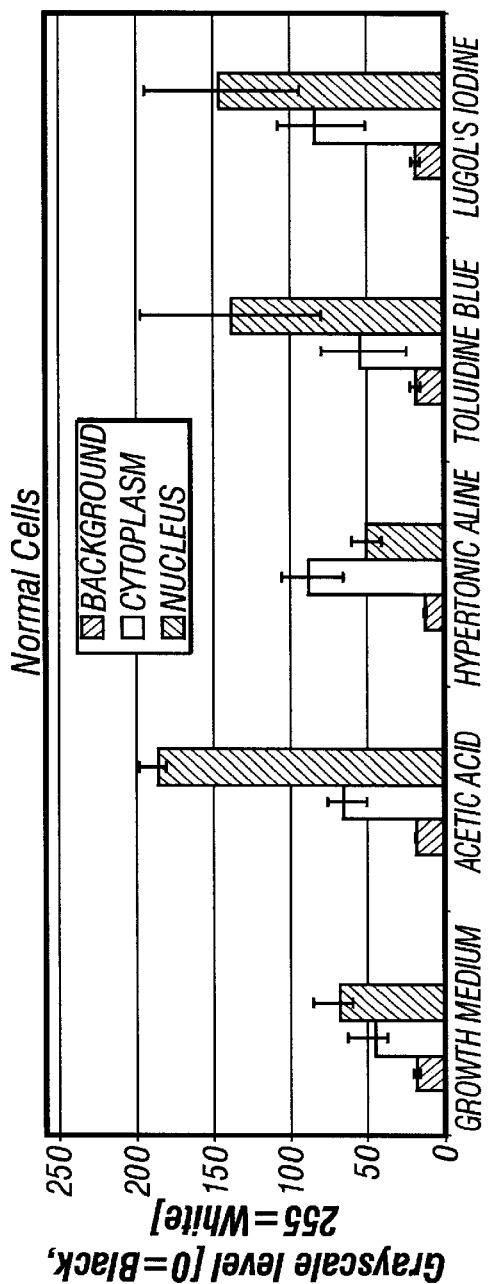
FIGS. 15A and 15B show the average grayscale levels for representative segments of the confocal images of normal cells (7 images for growth medium, 5 images for each contrast agent) (FIG. 15A). Also shown is the corresponding grayscale levels for the images of the cancer cells (10 images in all cases) (FIG. 15B). The error bars correspond to +/−one standard deviation.

All of the contrast agents used had an effect on the backscattering properties of cells, as viewed under reflectance confocal microscopy at 808 nm. In general, the addition of any of the agents resulted in increased backscattering from the cells and, in some cases, from different intracellular components. The results are summarized in FIG. 15. FIG. 15A shows the average grayscale values for representative regions of the confocal images of normal cells before and after the application of contrast agents. The error bars correspond to +/−1 standard deviation. The normal cells in growth medium have nuclei that are slightly brighter on average than the cytoplasm.

Adding acetic acid, toluidine blue and Lugol's iodine to normal cells increases the brightness of both the nucleus and cytoplasm. The relative differences between nucleus and cytoplasm are accentuated by acetic acid and toluidine blue. Toluidine blue and Lugol's iodine also increase the variability of the measurements, as evidenced by the larger standard deviations. Hypertonic saline solution makes the cytoplasm brighter than the nucleus in normal cells. The average brightness is changed the least by this agent.

Figure 15B:
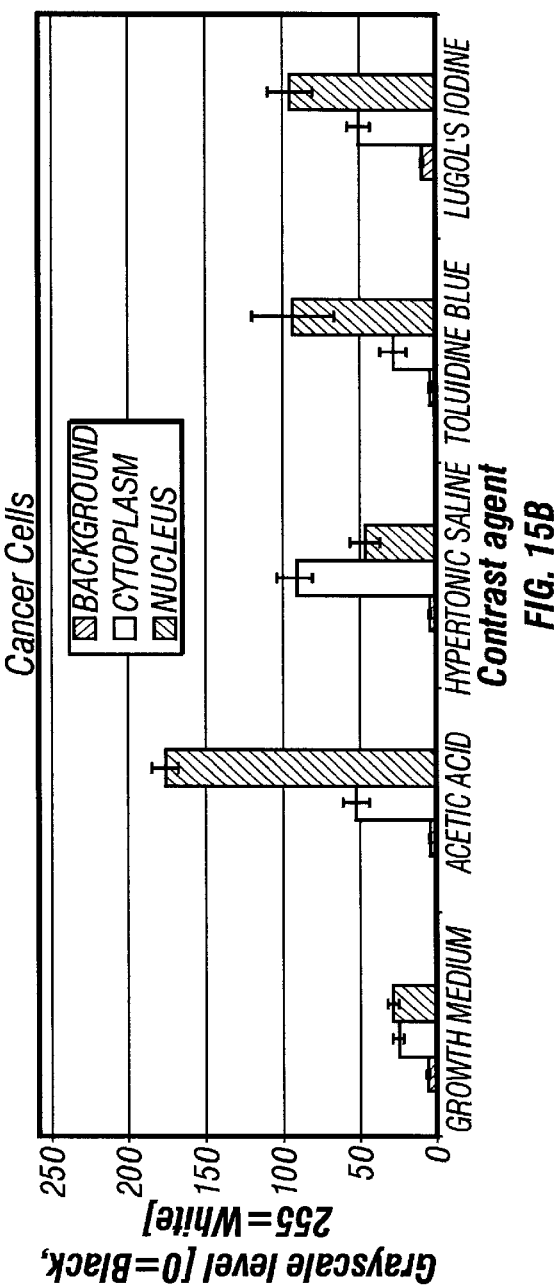

FIG. 15B shows the corresponding data for the cancer cells. Cancer cells in growth medium have almost identical brightness in the nucleus and cytoplasm. As with normal cells, acetic acid, toluidine blue and Lugol's iodine increase the overall scattering of the cells. At the same time, acetic acid and toluidine blue enhance the differentiation between the nucleus and cytoplasm within the cells by making the nucleus substantially brighter than the cytoplasm. An increase in the variability of the measurements is observed with toluidine blue and Lugol's iodine. Hypertonic saline solution increases the overall brightness of cancer cell images. However, this contrast agent causes the cytoplasm to be brighter than the nucleus.

Live normal and abnormal cells and tissues may have different uptake ratios for all of these chemicals, and this may further the ability of confocal microscopy to assess changes in cells and tissue. Furthermore, custom-made molecular agents, such as photodynamic therapy drugs, which are preferentially taken up and retained by cancer cells may also be useful in enhancing the diagnostic ability of in vivo confocal microscopy.

REFERENCES

The following references, to the extent that they provide exemplary procedural or other details supplementary to those set forth herein, are specifically incorporated herein by reference.

[1] "American Cancer Society Online. Cancer Facts & Figures-1997," in http://www.cancer.org/bottomcancinfo.html.
[2] S. L. Robbins, C. R. S., and V. Kumar, Pahtologic Basis of Disease. Philadelphia: W.B. Saunders Co., 1984.
[3] G. J. Kelloff, W. F. Malone, C. W. Boone, and e. al., "Intermediate Biomarkers of Precancers and their Application in Chemoprevention," Journal of Cellular Biochemistry, vol. Suppl(16G), pp. 15–21, 1992.
[4] T. R. Harrison and E. Braunwald, Harrison's Principles of Internal Medicine, vol. 1. New York: MacGraw-Hill, 1987.
[5] I. Burke, D. A. Antonioli, and B. S. Ducatman, Colposcopy, Text and Atlas. Norwalk, Conn.: Appleton and Large, 1991.
[6] S. Lam, C. MacAulay, and B. Palcic, "Detection and localization of early lung cancer by imaging techniques.," Chest., vol. 113, pp. 696–702, March. 1993,
[7] J. L. H. Evers and M. J. Heineman, Gynecology. A Clinical Atlas, 1 ed. Ontario: The C.V. Mosby Company, 1990.
[8] G. H. Anderson and e. al., "Organisation and Results of the Cervical Cytology Screening Programme in British Columbia, 1955–1985," British Medical Journal, vol. 296, pp. 975–978, 1988.
[9] M. T. Fahey, L. Irwig, and P. Macaskill, "Meta-analysis of Pap Test Accuracy," American Journal of Epidemiology, vol. 141, pp. 680–689, 1995.
[10] M. F. Mitchell, "The Accuracy of Colposcopy," Clinical Consultation in Obstetrics and Gynecology, vol. 6, pp. 70–73, 1994.
[11] N. Ramanujam, M. F. Mitchell, A. Mahadevan, and e. al., "Fluorescence Spectroscopy: a Diagnostic Tool for Cervical Intraepithelial Neoplasia (CIN)," Gynecologic Oncology, vol. 52, pp. 31–38, 1994.
[12] R. R. Alfano, G. C. Tang, A. Pradham, W. Lam, D. S. J. Choy, and E. Opher, "Fluorescence Spectra from Cancerous and Normal Human Breast and Lung Tissues," IEEE Journ. Quant. Electron., vol. QE-23, pp. 1806–1811, 1987.
[13] J. Hung, S. Lam, J. C. LeRiche, and B. Palcic, "Autofluorescence of normal and malignant bronchial tissue," Las. Surg. Med., vol. 11, pp. 99–105, 1991.
[14] K. Roy, D. R. Bottrill, D. R. Ingrams, and e. al., "Diagnostic Fluorescence Spectroscopy of Oral Mucosa," presented at Lasers and Surgery: Advanced Characterization, Therapeutics and Systems IV, SPIE, 1995.
[15] K. T. Schomacker, J. K. Frisoli, C. Compton, T. J. Flotte, J. M. Richter, N. Nishioka, and T. F. Deutsch, "Ultraviolet Laser-Induced Fluorescence of Colonic Tissue: Basic Biology and Diagnostic Potential," Las. Surg. Med., vol. 12, pp. 63–78, 1992.
[16] R. M. Cothren, R. Richards-Kortum, M. V. Sivak, M. Fitzmaurice, R. P. Rava, G. A. Boyce, M. Doxtader, R. Blackman, T. B. Ivanc, G. B. Hayes, M. S. Feld, and R. E. Petras, "Gastrointestinal tissue diagnosis by laser-induced fluorescence spectroscopy at endoscopy," Gastrointest. Endosc., vol. 36, pp. 105–111, 1990.
[17] N. S. Nishioka, "Laser-induced fluorescence spectroscopy. [Review]," Gastrointestinal Endoscopy Clinics of North America, vol. 4, pp. 313–326, 1994.
[18] R. Richards-Kortum and E. Sevick-Muraca, "Quantitative Optical Spectroscopy for Tissue Diagnosis," Annual Review in Physical Chemistry, vol. 47, pp. 555–606, 1996.
[19] A. G. Bohorfoush, "Tissue spectroscopy for gastrointestinal diseases. [Review]," Endoscopy, vol. 28, pp. 372–380, 1996.
[20] J. J. Bigio and J. R. Mourant, "Ultraviolet and visible spectroscopies for tissue diagnostics: fluorescence spectroscopy and elastic-scattering spectroscopy. [Review]," Physics in Medicine and Biology, vol. 42, pp. 803–814, 1997.
[21] J. Pawley, "Handbook of Biological Confocal Microscopy,". New York: Plenum Press, 1995.
[22] R. H. Webb, G. W. Hughes, and F. C. Delori, "Confocal Laser Scanning Ophtalmoscope," Applied Optics, vol. 26, pp. 1492–1499, 1987.
[23] C. Smithpeter, "Fiber optic confocal imaging for in vivo detection and diagnosis of pre-cancerous lesions,", 1997.
[24] S. Clivaz, F. Marquis-Weible, R. P. Salathe, R. P. Novak, and H. H. Gilgen, "High-Resolution Reflectometry in Biological Tissues," Opt. Lett., vol. 17, pp. 4, 1992.
[25] D. Huang, E. A. Swanson, C. P. Lin, J. S. Schuman, W. G. Stinson, W. Chang, M. R. Hoe, T. Flotte, K. Gregory, C. A. Puliafito, and J. G. Fujimoto, "Optical Coherence Tomography," Science, vol. 254, pp. 1178, 1991.
[26] J. A. Izatt, M. R. Hee, D. Huang, J. G. Fujimoto, E. A. Swanson, C. P. Lin, J. S. Schuman, and C. A. Puliafito, "Ophthalmic Diagnostics using Optical Coherence Tomography," Proc. Soc. Photo-Opt. Instrum. Eng., vol. 1877, pp. 136, 1993.
[27] E. A. Swanson, J. A. Izatt, M. R. Hee, D. Huang, C. P. Lin, J. S. Schuman, C. A. Puliafito, and J. G. Fujimoto, "In Vivo Measurements of Human Retinal Structure using Optical Coherence Tomography," Opt. Left., vol. 18, pp. 1864, 1993.
[28] R. C. Youngquist, S. Carr, and D. E. N. Davies, "Optical Coherence Domain Reflectometry: A New Optical Evaluation Technique," Opt. Lett., vol. 12, pp. 158, 1987.
[29] J. A. Izatt, M. R. Hee, D. Huang, E. A. Swanson, C. P. Lin, J. S. Schuman, C. A. Puliafito, and J. G. Fujimoto, "Micron-Resolution Biomedical Imaging with Optical Coherence Tomography," Opt. Photon. News, vol. 4, pp. 14, 1993.
[30] J. S. Schuman, M. R. Hee, C. A. Puliafito, C. Wong, T. Pedut-Kloizman, C. P. Lin, E. Hertzmark, J. A. Izatt, E. A. Swanson, and J. G. Fujimoto, "Quantification of Nerve Fiber Thickness in Normal and Glaucomatous Eyes using Optical Coherence Tomography: A Pilot Study," Arch. Ophthahnol., vol. 113, pp. 586–596, 1995.
[31] C. A. Puliafito, C. P. Lin, M. R. Hee, J. S. Schuman, J. S. Duker, E. Rachel, J. A. Izatt, E. A. Swanson, D. Huang, and J. G. Fujimoto, "Diagnostic of Macular Diseases with Optical Coherence Tomography," Ophthahnol., vol. 102, pp. 217–229, 1995.
[32] J. A. Izatt, M. R. Hee, E. A. Swanson, C. P. Lin, D. Huang, J. S. Schuman, C. A. Puliafito, and J. G. Fujimoto, "Micrometer-Scale Resolution Imaging of the Anterior Eye with Optical Coherence Tomography," Arch. Ophthalmol., vol. 112, pp. 1584–1589, 1995.
[33] M. R. Hee, J. A. Izatt, E. A. Swanson, D. Huang, J. S. Schuman, C. P. Lin, C. A. Puliafito, and J. G. Fujimoto, "Optical Coherence Tomography for Micron-Resolution Ophthalmic Imaging," in IEEE Eng. Med. Biol. Mag., vol. January/February, 1995, pp. 67–76.
[34] A. F. Fercher, K. Mengedoht, and W. Werner, "Eye-Length Measurement by Interferometry with Partially Coherent Light," Opt. Lett., vol. 13, pp. 186–188, 1988.

[35] J. A. Izatt, M. R. Hee, G. A. Owen, E. A. Swanson, and J. G. Fujimoto, "Optical Coherence Microscopy in Scattering Media," Opt. Lett., vol. 19, pp. 590–592, 1994.

[36] J. A. Izatt, H.-W. Wang, M. Kulkarni, K. Kobayashi, M. I. Canto, and M. V. Sivak, "Optical Coherence Tomography and Microscopy in Gastrointestinal Tissues," presented at Advances in Optical Imaging and Photon Migration, Orlando, FL, 1996.

[37] Y. Pan, R. Birngruber, J. Rosperich, and R. Engelhardt, "Low-Coherence Optical Tomography in Turbid Tissue: Theoretical Analysis," Appl. Opt., vol. 34, pp. 6564–6574, 1995.

[38] D. H. Reitze, S. Roper, F. I. Feldchtein, G. Gelikonov, N. D. Gladkova, V. M. Gelikonov, A. M. Sergeev, and N. M. Bityurin, "Low Coherence Imaging of Cerebral Structures in Vivo," presented at Coherence Domain Optical Methods in Biomedical Science and Clinical Applications, San Jose, Calif., 1997.

[39] J. M. Schmitt, A. Knuettel, and M. Yadlowsky, "Confocal Microscopy in Turbid Media," J. Opt. Soc. Am. A, vol. 11, pp. 2226–2235, 1994.

[40] G. J. Tearney, B. Bouma, S. A. Boppart, M. E. Brezinsky, J. F. Southern, E. A. Swanson, and J. G. Fujimoto, "Endoscopic Optical Coherence Tomography," presented at Optical Tomography and Spectroscopy of Tissue: Instrumentation, Model, and Human Studies II, San Jose, Calif., 1997.

[41] F. I. Feldchtein, G. V. Gelikonov, V. M. Gelikonov, R. V. Kuranov, and A. M. Sergeev, "Endoscopic applications of optical coherence tomography," Optics Express, vol. 3, pp. 257–270, 1998.

[42] Schmitt, "OCT elastography: imaging microscopic deformation and strain of tissue," Optics Express, vol. 6, pp. 199–211, 1998.

[43] J. de Boer, S. M. Srinivas, A. Malekafzali, Z. Chen, and J. S. Nelson, "Imaging thermally damagedd tissue by polarization sensitive optical coherence tomography," Optics Express, vol. 3, pp. 212–218, 1998.

[44] B. W. Colston, M. J. Everett, and H. Nathel, "Optical Coherence Tomography for Diagnosing Periodontal Disease," presented at Lasers in Denistry III, San Jose, CA, 1997.

[45] F. I Feldchtein, G. V. Gelikonov, V. M. I. Gelikonov, R.R., R. V. Kuranov, A. M. Sergeev, N. D. Gladkova, M. N. Ourutina, J. R. J. Warren, and D. H. Reitze, "In vivo OCT imaging of hard and soft tissue of the oral cavity," Optics Express, vol. 3, pp. 239–250, 1998.

[46] J. K. Barton, A. J. Welch, and J. A. Izaat, "Investigating pulsed dye laser-blood vessel interaction with color Doppler optical coherence tomography," Optcis Express, vol. 3, pp. 251–256, 1998.

[47] G. J. Tearney, S. A. Boppart, B. E. Bouma, M. E. Brezinsky, N. J. Weissman, J. F. Southern, and J. G. Fujimoto, "Scanning Single-Mode Fiber Optic Catheter-Endoscope for Optical Coherence Tomography," Opt. Lett., vol. 21, pp. 543–545, 1996.

[48] A. M. Sergeev, V. M. Gelikonov, G. V. Gelikonov, F. I. Feldchtein, R. V. Kuranov, N. D. Gladkova, and e. al., "In-vivo Endoscopic OCT Imaging of Precancer and Cancer States of Human Mucosa," Optics Express, vol. 1, pp. 432–4405 1997.

[49] C. Pitris, S. A. Boppart, B. E. Bouma, G. Tearney, J. G. Fujimoto, and M. E. Brezinski, "In-vivo catheter-based imaging with optical coherence tomography," presented at Advances in Optical Imaging and Photon Migration, Orlando, Fla., 1998.

[50] A. M. Rollins, M. D. Kulkami, S. Yazdanfar, R. Ung-arunyawee, and J. A. Izatt, "In vivo video rate optical coherence tomography," Optics Express, vol. 3, pp. 219–229, 1998.

[51] X. Clivaz, F. Marquis-Weible, and R. P. Salathe, "Optical Low Coherence Reflectometry with 1.9 $\mu$m Spatial Resolution," Electron. Lett., vol. 28, pp. 1553–1555, 1992.

[52] B. Bouma, G. J. Teamey, S. A. Boppart, and M. R. Hee, "High-Resolution Optical Coherence Tomographic Imaging Using a Mode-Locked Ti:Al2O3 Laser Source," Opt. Lett., vol. 20, pp. 1486–88, 1995.

[53] R. A. Drezek, A. Dunn, and R. Richards-Kortum, "Finite difference time domain modeling and goniometric measurements of light scattering form cells," Applied Optics, vol. 38, pp. 3651–3661, 1999.

[54] A. Sergeev, N. Gladkova, F. Feldchtein, V. Gelikonov, G. Gelikonov, L. Snopova, J. Ioannovich, K. Frangia, T. Pirza, I. Antoniu, A. Dunn, and R. Richards-Kortum, "Melanin effect on light scattering in tissues: from electrodynamics of living cell to OCT imaging," presented at Coherence Domain Optical Methods in Biomedical Science and Clinical Applications, 1997.

[55] A. F. Fercher, W. Drexler, C. K. Hitzenberger, and G. Kamp, "Measurement of Optical Distances by Optical Spectrum Modulation," presented at SPIE, 1994.

[56] M. A. Bail, G. Hausler, J. M. Herrmann, M. W. Lindner, and R. Ringler, "Optical coherence tomography with the "spectral radar": fast optical analysis in volume scatterers by short-coherence interferometry," presented at Photon Propagation in Tissues II, 1996.

[57] J. W. Goodman, Statistical Optics. New York: John Wiley and Sons, 1985.

[58] E. A. Swanson, D. Huang, M. R. Hee, J. G. Fujimoto, C. P. Lin, and C. A. Puliafito, "High Speed Optical Coherence Domain Reflectometry," Opt. Lett., vol. 17, pp. 151–153, 1992.

[59] J. M. Schmitt, A. Knuettel, and R. F. Bonner, "Measurement of Optical Properties of Biological Tissues by Low-Coehrence Reflectometry," Appl. Opt., vol. 32, pp. 6032–6042, 1993.

[60] A. F. Fercher, "New techniques in OCT," Conf Proc Laser Electr Optic Soc Annu Meet, pp. 54–55, 1997.

[61] M. R. Hee, J. A. Izatt, E. A. Swanson, D. Huang, J. S. Schuman, C. P. Lin, C. A. Puliafito, and J. G. Fujimoto, "Optical coherence tomography for ophthalmic imaging," IEEE Eng Med Biol, vol. 14, pp. 1–5, 1994.

[62] J. G. Fujimoto, M. E. Brezinsky, G. J. Tearney, S. A. Boppart, B. Bouma, M. R. Hee, J. F. Southern, and E. A. Swanson, "Optical Biopsy and Imaging Using Optical Coherence Tomography," Nature Medicine, vol. 1, pp. 970–972, 1995.

[63] A. F. Fercher, C. Hitzenberger, and M. Juchem, "Measurement of intraocular Optical Distances Using Partially Coherent Laser Light," Journal of Modern Optics, vol. 38, pp. 1327–1333, 1991.

[64] G. Hausler and M. W. Lindner, ""Coherence Radar" and "Spectral Radar" —New Tools for Dermatological Diagnosis," Journal of Biomedical Optics, vol. 3, pp. 21–31, 1998.

[65] U. Haberland, P. Jansen, V. Blazek, and H. J. Schmitt, "Optical Coherence Tomography of Scattering Media Using Frequency Modulated Continuous Wave Techniques with Tunable Near-infrared Laser," presented at SPIE, 1997.

[66] S. R. Chinn, E. A. Swanson, and J. G. Fujimoto, "Optical Coherence Tomography Using a Frequency-Tunable Optical Source," Optics Letters, vol. 22, pp. 340–342, 1997.

[67] M. Anderson, Jordon, J., Morse, A., and Sharp, F., A Text and Atlas of Integrated Colposcopy: Mosby, 1993.

[68] P. Sloot, A. Hoekstra, and C. Figdor, "Osmotic response of lymphocytes measured by means of forward light scattering: Theoretical considerations," Cytometry, vol. 9, pp. 636–641, 1988.

[69] S. Silverman, Jr., "Early diagnosis of oral cancer," Cancer, vol. 62, pp. 1796–9, 1988.

[70] M. Boon, and Drijver, J., Routine Cytological Staining Techniques. New York, N.Y.: Elsevier, 1986.

[71] A. F. Zuluaga, "Development of a cervical probe for optical coherence imaging in-vivo," in Dept. of Electrical and Computer Engineering. Austin: University of Texas at Austin, 1998, pp. 49.

[72] W. M. Coppenhaver, D. E. Kelly, and R. L. Wood, Bailey's Textbook of Histology, 17 ed. Baltimore: The Williams and Wilkins Company, 1978.

[73] P. Bernasconi, G. Montemezzani, M. Wintermantel, I. Biaggio, and P. Gunter, "High-resolution, high-speed photorefractive incoherent-to-coherent optical converter," Optics Letters, vol. 24, pp. 199–201, 1999.

[74] E. Hecht, Optics: Addison-Wesley, 1987.

[75] R. D. Guenther, Modem Optics, 1 ed. New York: John Wiley and Sons, 1990.

[76] M. Rajadhyaksha, M. Grossman, D. Esterwitz, R. Webb, and R. Anderson, "In-vivo confocal scanning laser microscope of human skin: melanin provides strong contrast," Journal of Investigative Dermatology, vol. 104, pp. 946–952, 1995.

[77] S. A. Boppart, G. J. Tearney, B. E. Bouma, J. F. Southern, M. E. Brezinski, and J. G. Fujimoto, "Noninvasive assessment of the developing Xenopus cardiovascular system using optical coherence tomography," Proceedings of the National Academy of Sciences of the United States of America, vol. 94, pp. 4256–4261, 1997.

[78] M. E. Brezinski, G. J. Tearney, B. Bouma, S. A. Boppart, C. Pitris, J. F. Southern, and J. G. Fujimoto, "Optical biopsy with optical coherence tomography," Annals of the New York Academy of Sciences, vol. 838, pp. 68–74, 1998.

[79] M. Bohnke and B. R. Masters, "Confocal microscopy of the cornea. [Review]," Progress in Retinal and Eye Research, vol. 18, pp. 553–628, 1999.

[80] B. E. Bouma and G. J. Tearney, "Power-efficient nonreciprocal interferometer and linear-scanning fiberoptic catheter for optical coherence tomography," Optics Letters, vol. 24, pp. 531–533, 1999.

[81] J. F. de Boer, T. E. Milner, and J. S. Nelson, "Determination of the depth-resolved Stokes parameters of light backscattered form turbid media by use of polarization-sensitive optical coherence tomography," Optics Letters, vol. 24, pp. 300–302, 1999.

[82] W. Hsing-Wen, J. Willis, M. J. F. Canto, M. V. Sivak, Jr., and J. A. Izatt, "Quantitative laser scanning confocal autofluorescence microscopy of normal, premalignant, and malignant colonic tissues," IEEE Transactions on Biomedical Engineering, vol. 46, pp. 1246–1252, 1999.

[83] C. Pitris, A. Goodman, S. Boppart, J. Libus, J. G. Fujimoto, and M. E. Brezinski, "High resolution imaging of gynecologic neoplasms using optical coherence tomography," Obstetrics and Gynecology, vol. 93, pp. 135–139, 1999.

[84] M. Rajadhyaksha, S. Gonzalez, J. M. Zavislan, R. R. Anderson, and R. H. Webb, "In vivo confocal scanning laser microscopy of human skin II: advances in instrumentation and comparison with histology," Journal of Investigative Dermatology, vol. 113, pp. 293–303, 1999.

[85] A. M. Rollins, R. Ung-arunyawee, A. Chak, R. C. K. Wong, K. Kobayashi, M. V. Sivak, Jr., and J. A. Izatt, "Real-time in vivo imaging of human gastrointestinal ultrastructure by use of endoscopic optical coherence tomography with a novel efficient interferometer design," Optics Letters, vol. 24, pp. 1358–1360, 1999.

[86] M. Tanifuji, M. Fukuda, and K. Tsunoda, "Functional imaging of the brain by using light," Oyo Buturi, vol. 68, pp. 997–1007, 1999.

[87] R. A. Drezek, T. Collier, C. K. Brookner, A. Malpica, R. Lotan, R. R. Richards-Kortum, and M. Follen, "Laser scanning confocal microscopy of cervical tissue before and after application of acetic acid," American Journal of Obstetrics and Gynecology, vol. 182, pp. 1135–1139, 2000.

[88] R. M. Zucker, A. P. Keshaviah, 0. T. Price, and J. M. Goldman, "Confocal laser scanning microscopy of rat follicle development," Journal of Histochemistry and Cytochemistry, vol. 48, pp. 781–791, 2000.

[89] A. Dunn and R. Richards-Kortum, "Three-dimensional computation of light scattering from cells," IEEE Journal of Selected Topics in Quantum Electronics, vol. 2, pp. 898–905, 1997.

[90] R. Schultz, and Skelton, H., "Value of acetic acid screening for flat genital condlyomata in men," Journal of Urology, vol. 139, pp. 777–779, 1988.

[91] G. Fiscor, Fuller, S., Jeromin, J., Beyer, D., and Janca, F., "Enhancing cervical cancer detection using nucleic acid hybridization and acetic acid tests," Nurse Practitioner, vol. 15, pp. 26–30, 1990.

[92] L. Van Le, F. Broekhuizen, R. Janzer-Steele, M. Behar, and T. Samter, "Acetic acid visualization of the cervix to detect cervical dysplasia," Obstetrics and Gynecology, vol. 81, pp. 293–295, 1993.

[93] J. Liu, Q. Wang, B. Li, X. Meng, Y. Zhang, X. Du, J. Yan, Y. Ping, and W. Li, "Superficial carcinomas of the esophagus and gastric cardia. A clinicopathological analysis of 141 cases," Chinese Medical Journal, vol. 108, pp. 754–759, 1995.

[94] R. H. Riddell, "Early detection of neoplasia of the esophagus and gastroesophageal junction," American Journal of Gastroenterology, vol. 91, pp. 853–863, 1996.

[95] V. Meyer, P. Burtin, B. Bour, A. Blanchi, P. Cales, F. Oberti, B. Person, A. Croue, S. Dohn, R. Benoit, B. Fabiani, and J. Boyer, "Endoscopic detection of early esophageal cancer in a high-risk population: does Lugol staining improve videoendoscopy?," Gastrointestinal Endoscopy, vol. 45, pp. 480–484, 1997.

[96] M. Derenzini, D. Trere, A. Pession, L. Montanaro, V. Sirri, and R. L. Ochs, "Nucleolar function and size in cancer cells," American Journal of Pathology, vol. 152, pp. 1291–1297, 1998.

[97] I. C. Martin, C. J. Kerawala, and M. Reed, "The application of toluidine blue as a diagnostic adjunct in the detection of epithelial dysplasia," Oral Surgery, Oral Medicine, Oral Pathology Oral Radiology and Endodontics, vol. 85, pp. 444–446, 1998.

[98] Y. Nakanishi, A. Ochiai, K. Yoshimura, H. Kato, T. Shimoda, H. Yamaguchi, Y. Tachimori, H. Watanabe, and S. Hirohashi, "The clinicopathologic significance of small areas unstained by Lugol's iodine in the mucosa surrounding resected esophageal carcinoma: an analysis of 147 cases," Cancer, vol. 82, pp. 1454–1459, 1998.

[99] C. Smithpeter, A. Duan, R. Drezek, T. Collier, and R. Richards-Kortum, "Near real time confocal microscopy of cultured amelanotic cells: sources of signal, contrast agents and limits of contrast," Journal of Biomedical Optics, vol. 3, pp. 429–436, 1998.

What is claimed is:

1. A method for enhancing contrast during imaging to assess cell and nuclear morphology of a sample, comprising:
   applying between about 0.5% and about 10% by volume of toluidine blue to the sample;
   analyzing the sample with a confocal microscope to create image data; and
   diagnosing the sample with the image data.

2. A method for enhancing contrast during imaging to enhance edges of cells of a sample, comprising:
   applying between about 2 to about 10 times physiological concentrations of hypertonic saline to the sample;
   analyzing the sample with an imaging device to create image data; and
   diagnosing the sample with the image data.

3. The method of claim 2, wherein the imaging device comprises a confocal microscope.

4. The method of claim 2, wherein the imaging device comprises an optical coherence tomography apparatus.

5. The method of claim 2, wherein the imaging device comprises a photon migration imaging device.

6. The method of claim 2, wherein the imaging device comprises a spectroscopy apparatus.

7. The method of claim 2, wherein the imaging device comprises a two-photon excited fluorescence imaging device.

8. The method of claim 6, wherein the spectroscopy comprises reflectance spectroscopy.

9. The method of claim 6, wherein the spectroscopy comprises absorption spectroscopy.

10. The method of claim 6, wherein the spectroscopy comprises fluorescence spectroscopy.

11. The method of claim 6, wherein the spectroscopy comprises Raman spectroscopy.

12. A method for enhancing contrast during imaging to enhance edges of cells of a sample, comprising:
    applying between about 0.1 to about 0.5 times physiological concentrations of hypotonic saline to the sample;
    analyzing the sample with an imaging device to create image data; and
    diagnosing the sample with the image data.

13. The method of claim 12, wherein the imaging device comprises a confocal microscope.

14. The method of claim 12, wherein the imaging device comprises an optical coherence tomography apparatus.

15. The method of claim 12, wherein the imaging device comprises a photon migration imaging device.

16. The method of claim 12, wherein the imaging device comprises a two-photon excited fluorescence imaging device.

17. The method of claim 12, wherein the imaging device comprises a spectroscopy apparatus.

18. The method of claim 17, wherein the spectroscopy comprises reflectance spectroscopy.

19. The method of claim 17, wherein the spectroscopy comprises absorption spectroscopy.

20. The method of claim 17, wherein the spectroscopy comprises fluorescence spectroscopy.

21. The method of claim 17, wherein the spectroscopy comprises Raman spectroscopy.

22. A method for enhancing contrast during imaging to assess cell and nuclear morphology of a sample, comprising:
    applying between about 5% and about 10% by volume of Lugol's iodine to the sample;
    analyzing the sample with a confocal microscope to create image data; and
    diagnosing the sample with the image data.

23. A method for enhancing contrast during imaging to assess cell and nuclear morphology of a sample, comprising:
    applying an absorbing dye comprising phycoerythrin or lutetium texaphyrin to the sample;
    analyzing the sample with an imaging device to create image data; and
    diagnosing the sample with the image data.

24. A method for enhancing contrast during imaging to assess cell and nuclear morphology of a sample, comprising:
    applying a liposome to the sample, the liposome containing a fluid of different refractive index;
    analyzing the sample with an imaging device to create image data; and
    diagnosing the sample with the image data.

25. The method of claim 9, wherein the fluid comprises water.

26. The method of claim 9, wherein the fluid comprises bovine serum albumin.

27. A method for enhancing contrast during imaging to assess cell and nuclear morphology of a sample, comprising:
    applying a contrast agent linked to a marker to the sample;
    analyzing the sample with an imaging device to create image data; and
    diagnosing the sample with the image data.

28. The method of claim 27, wherein the marker comprises CA125.

29. The method of claim 27, wherein the marker comprises EGFR.

30. The method of claim 27, wherein the marker comprises Her-2.

31. The method of claim 27, wherein the marker comprises Annexin-V.

32. The method of claim 27, wherein the marker comprises PCNA—proliferating cellular nuclear antigen.

33. The method of claim 27, wherein the marker comprises—endothelial growth factor receptor.

34. The method of claim 27, wherein the marker comprises VEGF—vascular endothelial growth factor.

35. The method of claim 27, wherein the marker comprises human milkfat protein.

36. The method of claim 27, wherein the marker comprises folate receptor.

37. A method for enhancing contrast during imaging to assess cell and nuclear morphology of a sample, comprising:
    applying between about 0.5% and about 10% by volume of toluidine blue to the sample;
    analyzing the sample with an imaging device to create image data, the imaging device comprising an optical coherence tomography apparatus, a photon migration imaging device, a two-photon excited fluorescence imaging device, an absorption spectroscopy apparatus, or a Raman spectroscopy apparatus; and
    diagnosing the sample with the image data.

38. A method for enhancing contrast during imaging to assess cell and nuclear morphology of a sample, comprising:
    applying between about 5% and about 10% by volume of Lugol's iodine to the sample;
    analyzing the sample with an imaging device to create image data; the imaging device comprising an optical coherence tomography apparatus, a photon migration imaging device, a two-photon excited fluorescence imaging device, an absorption spectroscopy apparatus, or a Raman spectroscopy apparatus; and
    diagnosing the sample with the image data.

* * * * *

UNITED STATES PATENT AND TRADEMARK OFFICE
CERTIFICATE OF CORRECTION

PATENT NO.     : 6,593,101 B2
DATED          : July 15, 2003
INVENTOR(S)    : Richards-Kortum et al.

It is certified that error appears in the above-identified patent and that said Letters Patent is hereby corrected as shown below:

<u>Column 24,</u>
Line 37, after "comprises", insert -- EGFR -- therefor.

Signed and Sealed this

Twenty-fifth Day of November, 2003

JAMES E. ROGAN
*Director of the United States Patent and Trademark Office*